US012636308B2

(12) United States Patent
Vaughn et al.

(10) Patent No.: US 12,636,308 B2
(45) Date of Patent: *May 26, 2026

(54) STORAGE STABLE FORMULATIONS OF SULFATED GLYCOSAMINOGLYCANS AND FRAGMENTS DERIVED THEREFROM FOR THE TREATMENT OF PAIN AND OTHER MEDICAL CONDITIONS

(71) Applicant: ADORA ANIMAL HEALTH CORPORATION, Franklin, TN (US)

(72) Inventors: Thomas Michael Vaughn, Franklin, TN (US); Joshua Alan Harrison, Jonesborough, TN (US); Karl F. Popp, Schodack Landing, NY (US); David J. Fairfax, Slingerlands, NY (US); Thomas Edward D'Ambra, Big Torch Key, FL (US); John Quinn, Troy, NY (US)

(73) Assignee: ADORA ANIMAL HEALTH CORPORATION, Franklin, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/187,241

(22) Filed: Apr. 23, 2025

(65) Prior Publication Data

US 2025/0249030 A1     Aug. 7, 2025

Related U.S. Application Data

(60) Continuation of application No. 18/750,691, filed on Jun. 21, 2024, now Pat. No. 12,303,528, which is a division of application No. 18/476,580, filed on Sep. 28, 2023, now Pat. No. 12,059,430.

(60) Provisional application No. 63/411,363, filed on Sep. 29, 2022.

(51) Int. Cl.
| | |
|---|---|
| *A61K 31/737* | (2006.01) |
| *A61K 9/00* | (2006.01) |
| *A61K 9/06* | (2006.01) |
| *A61K 45/06* | (2006.01) |
| *A61P 19/02* | (2006.01) |
| *A61P 29/00* | (2006.01) |

(52) U.S. Cl.
CPC .......... *A61K 31/737* (2013.01); *A61K 9/0014* (2013.01); *A61K 9/06* (2013.01); *A61K 45/06* (2013.01); *A61P 19/02* (2018.01); *A61P 29/00* (2018.01)

(58) Field of Classification Search
CPC .................................................. A61K 31/737
See application file for complete search history.

(56) References Cited

U.S. PATENT DOCUMENTS

| | | | |
|---|---|---|---|
| 4,524,066 | A | 6/1985 | Wolf |
| 5,036,056 | A | 7/1991 | Kludas |
| 6,339,074 | B1 | 1/2002 | Cialdi et al. |
| 6,388,060 | B1 | 5/2002 | Guo et al. |
| 6,541,460 | B2 | 4/2003 | Petito |
| 6,833,363 | B2 | 12/2004 | Renier et al. |
| 7,323,184 | B2 | 1/2008 | Freddo et al. |
| 7,544,368 | B2 | 6/2009 | Hsu et al. |
| 7,691,829 | B2 | 4/2010 | Petito et al. |
| 7,959,943 | B2 | 6/2011 | Hissong et al. |
| 7,976,873 | B2 | 7/2011 | Myntti et al. |
| 7,993,675 | B2 | 8/2011 | Oliver et al. |
| 8,088,095 | B2 | 1/2012 | Hissong et al. |
| 8,168,599 | B2 | 5/2012 | Petito et al. |
| 8,211,871 | B2 | 7/2012 | Gerrish |
| 8,258,191 | B2 | 9/2012 | Gerrish et al. |
| 8,486,374 | B2 | 7/2013 | Tamarkin et al. |
| 8,609,634 | B2 | 12/2013 | Doshi et al. |
| 8,685,439 | B2 | 4/2014 | Chapin et al. |
| 8,741,265 | B2 | 6/2014 | Tamarkin et al. |
| 8,795,654 | B2 | 8/2014 | Uvarkina et al. |
| 8,962,028 | B2 | 2/2015 | Johnson et al. |
| 8,993,536 | B2 | 3/2015 | Kakehi et al. |
| 9,125,892 | B2 | 9/2015 | Petito |
| 9,358,256 | B2 | 6/2016 | Devenish et al. |
| 9,402,857 | B2 | 8/2016 | Minatelli et al. |

(Continued)

FOREIGN PATENT DOCUMENTS

| | | | |
|---|---|---|---|
| BR | 112015022917 | A2 | 7/2017 |
| CH | 294894 | A | 11/1953 |

(Continued)

OTHER PUBLICATIONS

Volpi, Purification of heparin, dermatan sulfate and chondroitin sulfate from mixtures by sequential precipitation with various organic solvents. Journal of chromatography. B, Biomedical applications, (Oct. 11, 1996) vol. 685, No. 1, pp. 27-34 (Year: 1996).*
Definition of Chondroitin sulfate from Wikipedia , accessed on May 26, 2025, pp. 1-11 (Year: 2025).*
Wanitphakdeedecha et al., "The Effects of Mucopolysaccharide Polysulphate on Hydration and Elasticity of Human Skin," Dermatology Research and Practice 2011(2):807906 DOI: 10.1155/2011/807906.
White, G.W., "Adequan: A Review for the Practicing Veterinaria," Journal of Equine Veterinary Science 8(6):463-468 (1988).

(Continued)

*Primary Examiner* — Qiuwen Mi
(74) *Attorney, Agent, or Firm* — Troutman Pepper Locke LLP (Rochester)

(57) ABSTRACT

One aspect of the present application relates to a storage stable pharmaceutical composition comprising a sulfated glycosaminoglycan having an average molecular weight ranging from 3,000 to 15,000 Daltons, and a pharmaceutical carrier, where the pharmaceutical carrier is mixed with the sulfated glycosaminoglycan, as well as this composition's use in a method of treating a subject for a medically observable improvement. Another aspect of the present application relates to a process for producing a storage stable purified sulfated glycosaminoglycan.

36 Claims, No Drawings

(56) References Cited

U.S. PATENT DOCUMENTS

| | | | |
|---|---|---|---|
| 9,440,099 B2 * | 9/2016 | De Ambrosi | ........ A61K 31/727 |
| 9,579,341 B2 | 2/2017 | Doshi et al. | |
| 9,585,943 B2 | 3/2017 | Petito | |
| 9,782,458 B2 | 10/2017 | Petito | |
| 10,259,889 B2 | 4/2019 | Minamisawa et al. | |
| 10,413,595 B2 | 9/2019 | Stout et al. | |
| 10,471,106 B2 | 11/2019 | Petito | |
| 10,487,824 B2 | 11/2019 | Petito | |
| 11,071,758 B2 | 7/2021 | Petito | |
| 12,059,430 B2 | 8/2024 | Vaughn et al. | |
| 12,268,708 B2 | 4/2025 | Vaughn et al. | |
| 2003/0212005 A1 | 11/2003 | Petito et al. | |
| 2007/0110788 A1 | 5/2007 | Hissong et al. | |
| 2007/0264296 A1 | 11/2007 | Myntti | |
| 2009/0028926 A1 | 1/2009 | Grafe et al. | |
| 2009/0136598 A1 | 5/2009 | Chapin et al. | |
| 2010/0086576 A1 | 4/2010 | Myntti | |
| 2010/0173868 A1 | 7/2010 | Petito et al. | |
| 2010/0285102 A1 | 11/2010 | Angel | |
| 2014/0364369 A1 | 12/2014 | Ekre et al. | |
| 2015/0216788 A1 | 8/2015 | Petito | |
| 2015/0216947 A1 | 8/2015 | Petito | |
| 2016/0000858 A1 | 1/2016 | Tittl et al. | |
| 2016/0338935 A1 | 11/2016 | De Ambrosi et al. | |
| 2016/0367606 A1 | 12/2016 | Petito | |
| 2017/0290778 A1 | 10/2017 | Waugh | |
| 2018/0140709 A1 | 5/2018 | Chancey | |
| 2018/0333358 A1 | 11/2018 | Carlo | |
| 2019/0008795 A1 | 1/2019 | Waugh | |
| 2020/0023042 A1 | 1/2020 | Petito | |
| 2021/0340283 A1 | 11/2021 | Zhang et al. | |
| 2022/0143074 A1 | 5/2022 | Zhao et al. | |
| 2024/0342208 A1 | 10/2024 | Vaughn et al. | |

FOREIGN PATENT DOCUMENTS

| | | | |
|---|---|---|---|
| CN | 101891834 A | 11/2010 | |
| CN | 109970882 A | 7/2019 | |
| CN | 105288733 B | 10/2019 | |
| CN | 114451410 A | 5/2022 | |
| CN | 115105581 B | 11/2022 | |
| DE | 870094 C | 3/1953 | |
| DE | 102006049580 A1 | 4/2008 | |
| DE | 102007028360 B4 | 4/2016 | |
| DK | 2280720 T3 | 6/2019 | |
| EP | 1634893 B1 | 11/2007 | |
| ES | 2759373 T3 | 12/2009 | |
| JP | 3371207 B2 | 1/2003 | |
| JP | 2002293804 A | 10/2022 | |
| KR | 100827400 B1 | 5/2008 | |
| KR | 100938500 B1 | 1/2010 | |
| KR | 101134340 B1 | 4/2012 | |
| KR | 20150110332 A | 10/2015 | |
| KR | 101690539 B1 | 12/2016 | |
| KR | 102006036 B1 | 7/2019 | |
| WO | 2000056298 A2 | 9/2000 | |
| WO | WO-0056298 A2 * | 9/2000 | ........... A61K 31/726 |
| WO | 2003094937 A1 | 11/2003 | |
| WO | 2004044009 A1 | 5/2004 | |
| WO | 2006089167 A1 | 8/2006 | |
| WO | 2008148873 A2 | 12/2008 | |
| WO | 2009013162 A1 | 1/2009 | |
| WO | 2009061431 A2 | 5/2009 | |
| WO | 2009089368 A1 | 7/2009 | |
| WO | 2010028087 A2 | 3/2010 | |
| WO | 2010129547 A1 | 11/2010 | |
| WO | 2012122956 A1 | 9/2012 | |
| WO | 2012146655 A1 | 11/2012 | |
| WO | 2012154953 A2 | 11/2012 | |
| WO | 2014017145 A1 | 1/2014 | |
| WO | 2014078446 A2 | 5/2014 | |
| WO | 2015164822 A1 | 10/2015 | |
| WO | 2017032856 A2 | 3/2017 | |
| WO | 2018029340 A1 | 2/2018 | |
| WO | 2019010484 A2 | 1/2019 | |
| WO | 2021107067 A1 | 6/2021 | |
| WO | 2022034078 A1 | 2/2022 | |

OTHER PUBLICATIONS

Oryan et al., "Response of a Collagenase-Induced Tendon Injury to Treatment with a Polysulphated Glycosaminoglycan (Adequan)," Connective Tissue Research 49(5):351-360 (2008) (Abstract).

Adequan Canine, About Adequan Canine, American Regent Animal Health, Shirley, NY, USA, American Regent Animal Health (Aug. 10, 2021) https://adequancanine.com/?utm_source=scripps&utm_medium=sem&utm_campaign=aboutadequancanine&utm_content=aboutadequancanine&gclid=EAlalQobChMInZ_r9syn8gIVEs53Ch0M5w1QEAAYASAAEglJgPD_B.

Adequan Equine, "Adequan i.m.—The Only FDA-approved Equine PSGAG," American Regent Animal Health, Shirley, NY, USA, American Regent Animal Health (Aug. 10, 2021) https://www.adequan.com/?utm_source=scripps&utm_medium=sem&utm_content=about&gclid=EAlalQobChMInZ_r9syn8gIVEs53Ch0M5w1QEAAYAiAAEgLPHfD_BwE.

Gulpinar et al., "Clinical Comparison of Intravesical Hyaluronic Acid And Chondroitin Sulfate Therapies in the Treatment of Bladder Pain Syndrome/Interstitial Cystitis," Neurourol Urodyn. 37(1):257-262 (2018).

Colemeadow et al., "Clinical Management of Bladder Pain Syndrome/Interstitial Cystitis: A Review on Current Recommendations and Emerging Treatment Options," Res Rep Urol. 12:331-343 (2020).

De Vita et al., "Effectiveness of Intravesical Hyaluronic Acid With or Without Chondroitin Sulfate for Recurrent Bacterial Cystitis in Adult Women: A Meta-Analysis," International Urogynecology Journal 24(4):545-552 (2012).

Lu et al., "Characteristic Oligosaccharides Released from Acid Hydrolysis for the Structural Analysis of Chondroitin Sulfate," Carbohydrate Research, 449:114-119 (2017).

Hmingthansanga et al., "Improved Topical Drug Delivery: Role of Permeation Enhancers and Advanced Approaches," Pharmaceutics, 14(12):2818 (2022).

Walters and Hadgraft, "Pharmaceutical Skin Penetration Enhancement," Marcel Dekker, Inc., New York (1993).

Osborne and Henke, "Skin Penetration Enhancers Cited in the Technical Literature," Pharm. Technology, 21:58-66 (1997).

Thong et al., "Percutaneous Penetration Enhancers: An Overview." Skin Pharmacology & Physiology, 20(6):272-82 (2007).

Watt and Gulati, "New Drug Treatments for Osteoarthritis: What is on the Horizon?," Eur Med J Rheumatol., 2(1):50-58 (2017).

Wang et al., "Glycosaminoglycans: Sweet as Sugar Targets for Topical Skin Anti-Aging," Clinial, Cosmetic and Investigational Dermatology, 14:1227-1246 (2021).

Hoppensteadt et al., "Comparative Studies on the Topical Administration of Mucopolysaccharide and Heparin Ointments in Nonhuman Primates," Clinical and Applied Thrombosis/Hemostasis, 16(1):13-20 (2010).

Yao et al., "A Topical Heparinoid-Containing Product Improves Epidermal Permeability Barrier Homeostasis in Mice," Exp Dermatol, 28(8):956-960 (2019).

Vecchio and Frisinghelli, "Topically Applied Heparins for the Treatment of Vascular Disorders: A Comprehensive Review," Clin Drug Investig, 28(10):603-614 (2008).

Thrombocid 1 MG/G Cream Ointment 30 G, Parafarmacia-online. com (retrieved Dec. 5, 2023) https://www.parafarmacia-online.com/en/thrombocid-1-mg-g-ointment-cream-30-g.

Hirudoid Forte® Mucopolysaccharide Cream, Okdermo.com (retrieved Dec. 5, 2023) https://okdermo.com/product/mucopolysaccharide-polysulphate-40000-u-organo-heparinoid-luitpold-cream-hirudoid-forte-40g/.

Hirudoid Cream, Electronic Medicines Compendium (retrieved Dec. 5, 2023) https://www.medicines.org.uk/emc/product/1341/smpc#gref.

Hirudoid Forte Cream 40g, THAIEGOU (retrieved Dec. 5, 2023) http://shop5.thaiegou.com/index.php?route=product/product&product_id=156.

(56)     References Cited

OTHER PUBLICATIONS

Pentosan Polysulfate Sodium 1 mg/Gm Topical Cream, (retrieved Dec. 6, 2023) https://www.bayviewrx.com/formulas/Pentosan-Polysulfate-Sodium-1-mg-Gm-Topical-Cream-Interstitial-Cystitis-Osteoarthritis-Urethral-Syndrome-Bladder-Pain-Syndrome-Hemorrhoids-.

Hirudoid®, Medinova (retrieved Dec. 5, 2023) https://www.medinova.ch/en/products/hirudoid/.

"Potential New Treatment for Osteoarthritis", Osteoarthritis Blog, Arthritis Foundation (retrieved Dec. 5, 2023) http://blog.arthritis.org/osteoarthritis/new-osteoarthritis-treatments/.

"Arthritis Pain: Treatments Absorbed Through Your Skin," Mayo Clinic (retrieved Dec. 5, 2023) https://www.mayoclinic.org/diseases-conditions/osteoarthritis/in-depth/pain-medications/art-20045899.

Hirudoid® Heals Bruises, (retrieved Dec. 5, 2023) https://hirudoid.com.au/hirudoid.com.au/index.html.

Wikipedia, "Polysulfated Glycosaminoglycan," Dec. 21, 2020, retrieved on Feb. 8, 2024 from https://en.wikipedia.org/w/index.php?title=Polysulfated_glycosaminoglycan&oldid=995549530.

International Search Report and Written Opinion for PCT/US2023/033947, dated Mar. 12, 2024.

Non-Final Office Action in U.S. Appl. No. 18/476,580, mailed Feb. 27, 2024.

Xioglican™ Cream and Xioglican™ Gel product data sheets, available from Neopharmed Gentili S.p.A. (Milan, Italy) at https://www.ospitalitymed.com/neogen/d/vascolare/dispositivi-medici/xioglican/69/ (last revised Jan. 2018; accessed Dec. 2024).

ICHON Material Safety Data Sheet, available from Kinetic Technologies LLC (Lexington, KY) at https://northamerica.covetrus.com/Content/SDS/041229.pdf (issued Jan. 26, 2010; accessed Jan. 8, 2025).

Leite et al., "Skin Delivery of Glucosamine and Chondroitin Sulphates—A Perspective on the Conservative Treatment for Osteoarthritis of the Knee," Journal of Biosciences and Medicines 5(4):11-20 (2017).

Non-Final Office Action in U.S. Appl. No. 18/757,390, mailed Aug. 29, 2024.

Non-Final Office Action in U.S. Appl. No. 18/750,691, mailed Nov. 15, 2024.

Final Office Action in U.S. Appl. No. 18/750,691, mailed Jan. 28, 2025.

Autotranslation of Hirudoid® forte cream product information sheet, Medinova AG (Nov. 2021).

Definition of heparan sulfate from Wikepedia, accessed on Jun. 25, 2025, pp. 1-12 (Year: 2025).

* cited by examiner

STORAGE STABLE FORMULATIONS OF SULFATED GLYCOSAMINOGLYCANS AND FRAGMENTS DERIVED THEREFROM FOR THE TREATMENT OF PAIN AND OTHER MEDICAL CONDITIONS

This application is a continuation of U.S. patent application Ser. No. 18/750,691, filed Jun. 21, 2024, which is a divisional of U.S. patent application Ser. No. 18/476,580, filed Sep. 28, 2023, now issued as U.S. Pat. No. 12,059,430, which claims the benefit of U.S. Provisional Patent Application Ser. No. 63/411,363, filed Sep. 29, 2022, which is hereby incorporated by reference in its entirety.

FIELD

The present application relates to storage stable formulations of sulfated glycosaminoglycans and fragments derived therefrom for the treatment of pain and other medical conditions.

BACKGROUND

Osteoarthritis (OA) is the most common form of arthritis, causing enormous suffering and healthcare cost; one-third of those aged >45 years seek treatment for OA and 81% of these have constant pain or limitation of activities (Arthritis Research UK, "Osteoarthritis in General Practice: Data and Perspectives,". (Last accessed: 17 Jan. 2017) (2013). The majority of joint replacements can be attributed to OA pain. By 2030, it is expected that 560,000 hip replacements each year will occur within the USA (Neogi T., "The Epidemiology and Impact of Pain in Osteoarthritis," *Osteoarthritis Cartilage.* 21(9):1145-53 (2013)). This being said, OA has historically lagged rheumatoid arthritis (RA) in levels of research and drug development. With an ageing and increasingly obese population, incidence of symptomatic OA and joint replacements are increasing year-on-year, associated with increasingly unsustainable costs (Losina et al., "Lifetime Medical Costs of Knee Osteoarthritis Management in the United States: Impact of Extending Indications for Total Knee Arthroplasty," *Arthritis Care Res.* 67(2):203-15 (2015)). OA is now becoming a disease seen in younger people, in their 40s and 50s, who are not yet appropriate for joint arthroplasty. This has led to a clear and increasing unmet need for new pharmacological treatments.

Osteoarthritis results from loss of cartilage that normally protects the joints, leading to pain, swelling and stiffness. OA is a progressive disease, and as cartilage erodes over time, the symptoms will worsen. As there is currently no cure for the disease, standard treatment for OA involves managing these symptoms. The primary pharmacological treatments for the symptoms of OA are analgesics, including acetaminophen, nonsteroidal anti-inflammatory drugs (NSAIDs), and opioid medications (Conaghan et al., "Treating Osteoarthritis Pain: Recent Approaches Using Pharmacological Therapies," *Clin. Exp. Rheumatol.* 37 Suppl 120 (5):S124-29 (2019)). Acetaminophen is typically the recommended first line analgesic of choice, and when successful, the preferred long-term analgesic due to its favorable safety profile compared to NSAIDs (Zang et al., "EULAR Evidence Based Recommendations for the Management of Hip Osteoarthritis: Report of a Task Force of the EULAR Standing Committee for International Clinical Studies Including Therapeutics (ESCISIT)," *Ann. Rheum. Dis.* 64(5):669-81 (2005)). However, acetaminophen has been linked to an increased risk of hepatic, hypertensive, and cardiovascular adverse effects (Chan, et al., "Nonsteroidal Antiinflammatory Drugs, Acetaminophen, and the Risk of Cardiovascular Events," *Circulation.* 113(12):1578-87 (2006); Pincus et al., *Ann. Rheum. Dis.* 63(8):931-9 (2004)). NSAIDs provide analgesic, anti-inflammatory, and anti-pyretic effects, but are associated with potential side effects, including gastrointestinal events (e.g., bleeding, inflammation, ulcers, etc.) and cardiovascular events (e.g., myocardial infarction and stroke) (Antman et al., "Use of Nonsteroidal Anti-inflammatory Drugs: An update for Clinicians: A Scientific Statement from the American Heart Association," *Circulation* 115(12):1634-42 (2007)). In cases where acetaminophen and NSAIDs are not effective in treating pain from OA, opioid analgesics may be employed, but their use is limited due to potential serious adverse effects, which include constipation, respiratory depression, tolerance, and dependence (Grässel et al., "Recent Advances in the Treatment of Osteoarthritis," *F1000Res.* 9: F1000 Faculty Rev-325 (2020)). Intra-articular and intramuscular corticosteroid injections are also commonly used to relieve the symptoms of OA, but this treatment often provides only short-term benefits (Conaghan et al., "Treating Osteoarthritis Pain: Recent Approaches Using Pharmacological Therapies," *Clin. Exp. Rheumatol.* 37 Suppl 120(5):S124-29 (2019)). When these non-invasive treatments fail, surgical options such as joint replacement are often considered.

In addition to joint damage caused by arthritis, normal function of a joint and its movement, and other portions of the body, can be severely impaired as a result of trauma or following orthopedic and other surgical procedures. Human joints, in particular the knee, ankle, hip, elbow, wrist, knuckle and spine, are susceptible to degeneration from disease, trauma, and long-term repetitive use that eventually lead to pain. This impairment may result in tenderness, aching, pain, and lengthy recovery times, as well as loss of joint mobility or reduced range of motion, tonicity, or elasticity of the joint/articular structures, such as for example, muscle, tendon, capsule, bone, or ligament. Reduced joint mobility may also involve permanently altered or shortened joint or tissue architecture. Altered or abnormal joint mobility or joint architecture may also be associated with or caused by a variety of injuries and conditions such as metabolic disorders, ischemia, injury to joint, capsule, bone, cartilage, tendon, ligament or muscle, fractures, subluxation, dislocation, crush injuries, prolonged immobilization (e.g., immobilization of a joint in a cast or splint), and paralysis. Like osteoarthritis, current evidence-based guidelines support pharmacological treatment of these other forms of joint damage with acetaminophen or oral NSAIDs to reduce pain and inflammation. Due to the potential side effects of these analgesics, there is a need for other treatment options for pain occurring as a result of osteoarthritis, as well as other types of joint degeneration, soft tissue injury, muscle soreness, etc. Furthermore, these analgesics only treat symptoms. There is a need for treatment that not only relieves symptoms but has a disease modifying effect that improves the underlying cause(s) of this condition and can potentially reverse damage.

Topical pain relievers are used to relieve pain, such as that associated with arthritis, as well as pain, joint stiffness, and muscle soreness caused by sports injuries or other physical activity. However, such topically applied therapeutics are associated with adverse effects including skin rash, nausea, vomiting, heartburn, gas, diarrhea, constipation, and stomach pain.

The present application is directed to alleviating deficiencies in prior treatments.

SUMMARY

One aspect of the present application relates to a storage stable pharmaceutical composition comprising a sulfated glycosaminoglycan having an average molecular weight ranging from 3,000 to 15,000 Daltons, a skin penetrating agent, where the skin penetrating agent promotes transdermal penetration of the sulfated glycosaminoglycan when applied to intact skin surfaces, and a pharmaceutical carrier for topical application, where the pharmaceutical carrier is mixed with the sulfated glycosaminoglycan and the skin penetrating agent.

Another aspect of the present application relates to a method of treating a subject for pain, joint stiffness, soft tissue injury, connective tissue disorders, and/or muscle soreness. This method comprises selecting a subject in need of treatment for pain, joint stiffness, soft tissue injury, connective tissue disorders, and/or muscle soreness; administering to the selected subject a storage stable pharmaceutical composition comprising a sulfated glycosaminoglycan having an average molecular weight ranging from 3,000 to 15,000 Daltons, a skin penetrating agent, where the skin penetrating agent promotes transdermal penetration of the sulfated glycosaminoglycan when applied to intact skin surfaces, and a pharmaceutical carrier for topical application, where the pharmaceutical carrier is mixed with the sulfated glycosaminoglycan and the skin penetrating agent. The administering is carried out topically at a location proximate to where the subject is experiencing pain, joint stiffness, soft tissue injury, connective tissue disorders, and/or muscle soreness.

Another aspect of the present application relates to a storage stable sulfated glycosaminoglycan having an average molecular weight ranging from 3,000 to 15,000 Daltons.

Another aspect of the present application relates to a storage stable pharmaceutical composition comprising a sulfated glycosaminoglycan having an average molecular weight ranging from 3,000 to 15,000 Daltons, and a pharmaceutical carrier, where the pharmaceutical carrier is mixed with the sulfated glycosaminoglycan.

Another aspect of the present application relates to a method of treating a subject for a medically observable improvement. This method comprises selecting a subject in need of treatment for a medically diagnosable condition and administering to the selected subject a storage stable pharmaceutical composition comprising a sulfated glycosaminoglycan having an average molecular weight ranging from 3,000 to 15,000 Daltons and a pharmaceutical carrier to facilitate treatment, where the pharmaceutical carrier is mixed with the sulfated glycosaminoglycan.

Another aspect of the present application relates to a process for producing a storage stable purified sulfated glycosaminoglycan. This process comprises providing a sulfated glycosaminoglycan starting material containing components below 1,000 Daltons, subjecting the sulfated glycosaminoglycan starting material to tangential flow filtration under conditions effective to reduce the amount of components below 1,000 Daltons in the starting material to produce a purified sulfated glycosaminoglycan having an average molecular weight ranging from 3,000 to 15,000 Daltons, wherein the purified sulfated glycosaminoglycan includes no more than 10 wt % of carbohydrates or other contaminants with a molecular weight below 1,000 Daltons, and recovering the purified sulfated glycosaminoglycan.

The present application relates to composition for the treatment of various conditions, including the treatment of joint pain, soft tissue injury, connective tissue disorders and muscle soreness in a human or animal body. The method includes preparing a therapeutic composition from a mixture of polysulfated glycosaminoglycan fragments derived from chondroitin sulfate, in some cases with a skin penetration agent. The method also embodies administering the therapeutic composition to the human or animal body, including topically applying it proximate to where a person or animal is experiencing discomfort or injury. Furthermore, the method includes the use of topical compositions that employ creams, gels, excipients, transdermal tapes and patches, ointments, gels, pastes or collodions. A combination of the polysulfated glycosaminoglycan fragments with pharmaceutically acceptable free bases, salts, esters, ethers, or solvates of antibiotics, anti-infectives, antimycotics agents, steroids, cannabinoids, antihistamines, anti-inflammatory agents, antiparasitic agents, immunomodulators, antisense agents, antiviral agents, treatments for hyper- and hypo skin pigmentation disorders, anti-psoriatic agents, keratolytic agents, DNA synthesis inhibitors, cytotoxic agents, antithyroid agents, monoclonal antibody regulators, TNF alpha antagonists, immunoglobulins, metabolic regulators, antiangiogenic agents, protease inhibitors, anxiolytics, kinase regulators, cell growth regulators, enzymes, prostaglandins, peptides, analgesics, skin moisturizers, astringents, exfoliating agents, agents intended to protect the skin, modify its appearance, or improve its rate of healing, and/or combinations thereof, including various active or synergistic ingredients, such as lidocaine (and other local anesthetics), DMSO, glucosamine, diclofenac, capsaicin, salicylates, CBD, THC, menthol and other ingredients is also disclosed.

The method also embodies a process for purifying polysulfated glycosaminoglycan fragments to remove lower molecular weight by-products and impurities by procedures, such as ultrafiltration or diafiltration. This purification method results in purified polysulfated glycosaminoglycans that can be used to prepare therapeutic compositions with enhanced shelf life compared to formulations containing polysulfated glycosaminoglycans that are not prepared by this process.

Current treatments for these ailments are limited in that they focus on treating symptoms such as joint and/or muscle pain and stiffness as well as limitations to range of motion. Often these treatments, while effective short term in alleviating pain, may exacerbate disease progression leading to a steady worsening of condition over time. At this time, there are no pharmacological agents widely available that are safe, easy to administer and capable of retarding the progression of or preventing osteoarthritis.

Considerable research on glycosaminoglycans support their potential utility in alleviating pain and slowing disease progression in osteoarthritis. However, these high molecular weight compounds have only shown benefit when administered by injection—due to their very high molecular weights and highly charged ionic structures. Furthermore, methods to prepare pharmaceutically acceptable sulfated glycosaminoglycans such as PSGAG have been difficult to reproduce and lead to product contaminated with lower molecular weight by-products and impurities that have limited the utility of this class of agents.

The present application discloses how to overcome these limitations, by use of PSGAGs within defined molecular weight ranges. These can be used effectively to treat a number of conditions in different ways, including allowing patients to easily apply a topical formulation that includes skin penetrating enhancers that facilitate delivery of such an active ingredient through the skin barriers, allowing the active ingredient to reach the site of action without the need for injection.

DETAILED DESCRIPTION

One aspect of the present application relates to a storage stable pharmaceutical composition comprising a sulfated glycosaminoglycan having an average molecular weight ranging from 3,000 to 15,000 Daltons, a skin penetrating agent, where the skin penetrating agent promotes transdermal penetration of the sulfated glycosaminoglycan when applied to intact skin surfaces, and a pharmaceutical carrier for topical application, where the pharmaceutical carrier is mixed with the sulfated glycosaminoglycan and the skin penetrating agent.

In some embodiments, the sulfated glycosaminoglycan is selected from the group consisting of chondroitin sulfate, mucopolysaccharide polysulfate, polysulfated glycosaminoglycan, and/or combinations thereof. In some embodiments, the sulfated glycosaminoglycan comprises chondroitin sulfate. In some embodiments, the sulfated glycosaminoglycan comprises less than 5 wt % of chondroitin sulfate. For example, in some embodiments, the sulfated glycosaminoglycan comprises less than 0.5 wt %, less than 1 wt %, less than 1.5 wt %, less than 2 wt %, less than 2.5 wt %, less than 3 wt %, less than 3.5 wt %, less than 4 wt %, or less than 4.5 wt %. In some embodiments, the sulfated glycosaminoglycan comprises mucopolysaccharide polysulfate. In other embodiments, the sulfated glycosaminoglycan comprises polysulfated glycosaminoglycan.

As described herein, a sulfated glycosaminoglycan includes sulfated naturally occurring glycosaminoglycans of full length as well as sulfated fragments of these polyglycans derived through chemical or enzymatic manipulation, where the average molecular weight of the sulfated glycosaminoglycan fragments is 3,000 to 15,000 Da. For example, in some embodiments, the average molecular weight of the sulfated glycosaminoglycan fragments is 3,000 to 4,000 Da, 3,000 to 5,000 Da, 3,000 to 6,000, 3,000 to 7,000 Da, 3,000 to 8,000 Da, 3,000 to 9,000 Da, 3,000 to 10,000 Da, 3,000 to 11,000 Da, 3,000 to 12,000 Da, 3,000 to 13,000 Da, 3,000 to 14,000 Da, 3,000 to 15,000 Da, 3,500 to 4,000 Da, 3,500 to 5,000 Da, 3,500 to 6,000, 3,500 to 7,000 Da, 3,500 to 8,000 Da, 3,500 to 9,000 Da, 3,500 to 10,000 Da, 3,500 to 11,000 Da, 3,500 to 12,000 Da, 3,500 to 13,000 Da, 3,500 to 14,000 Da, 3,500 to 15,000 Da, 4,000 to 5,000 Da, 4,000 to 6,000, 4,000 to 7,000 Da, 4,000 to 8,000 Da, 4,000 to 9,000 Da, 4,000 to 10,000 Da, 4,000 to 11,000 Da, 4,000 to 12,000 Da, 4,000 to 13,000 Da, 4,000 to 14,000 Da, 4,000 to 15,000 Da, 4,500 to 5,000 Da, 4,500 to 6,000 Da, 4,500 to 7,000 Da, 4,500 to 8,000 Da, 4,500 to 9,000 Da, 4,500 to 10,000 Da, 4,500 to 11,000 Da, 4,500 to 12,000 Da, 4,500 to 13,000 Da, 4,500 to 14,000 Da, 4,500 to 15,000 Da, 5,000 to 6,000 Da, 5,000 to 7,000 Da, 5,000 to 8,000 Da, 5,000 to 9,000 Da, 5,000 to 10,000 Da, 5,000 to 11,000 Da, 5,000 to 12,000 Da, 5,000 to 13,000 Da, 5,000 to 14,000 Da, 5,000 to 15,000 Da, 5,500 to 6,000 Da, 5,500 to 7,000 Da, 5,500 to 8,000 Da, 5,500 to 9,000 Da, 5,500 to 10,000 Da, 5,500 to 11,000 Da, 5,500 to 12,000 Da, 5,500 to 13,000 Da, 5,500 to 14,000 Da, 5,500 to 15,000 Da, 6,000 to 7,000 Da, 6,000 to 8,000 Da, 6,000 to 9,000 Da, 6,000 to 10,000 Da, 6,000 to 11,000 Da, 6,000 to 12,000 Da, 6,000 to 13,000 Da, 6,000 to 14,000 Da, 6,000 to 15,000 Da, 6,500 to 7,000 Da, 6,500 to 8,000 Da, 6,500 to 9,000 Da, 6,500 to 10,000 Da, 6,500 to 11,000 Da, 6,500 to 12,000 Da, 6,500 to 13,000 Da, 6,500 to 14,000 Da, 6,500 to 15,000 Da, 7,000 to 8,000 Da, 7,000 to 9,000, 7,000 to 9,500 Da, Da, 7,000 to 10,000 Da, 7,000 to 11,000 Da, 7,000 to 12,000 Da, 7,000 to 13,000 Da, 7,000 to 14,000 Da, 7,000 to 15,000 Da, 7,500 to 8,000 Da, 7,500 to 9,000 Da, 7,500 to 10,000 Da, 7,500 to 11,000 Da, 7,500 to 12,000 Da, 7,500 to 13,000 Da, 7,500 to 14,000 Da, 7,500 to 15,000 Da, 8,000 to 9,000 Da, 8,000 to 10,000 Da, 8,000 to 11,000 Da, 8,000 to 12,000 Da, 8,000 to 13,000 Da, 8,000 to 14,000 Da, 8,000 to 15,000 Da, 8,500 to 9,000 Da, 8,500 to 10,000 Da, 8,500 to 11,000 Da, 8,500 to 12,000 Da, 8,500 to 13,000 Da, 8,500 to 14,000 Da, 8,500 to 15,000 Da, 9,000 to 10,000 Da, 9,000 to 11,000 Da, 9,000 to 12,000 Da, 9,000 to 13,000 Da, 9,000 to 14,000 Da, 9,000 to 15,000 Da, 9,500 to 10,000 Da, 9,500 to 11,000 Da, 9,500 to 12,000 Da, 9,500 to 13,000 Da, 9,500 to 14,000 Da, 9,500 to 15,000 Da, 10,000 to 11,000 Da, 10,000 to 12,000 Da, 10,000 to 13,000 Da, 10,000 to 14,000 Da, 10,000 to 15,000 Da, 10,500 to 11,000 Da, 10,500 to 12,000 Da, 10,500 to 13,000 Da, 10,500 to 14,000 Da, 10,500 to 15,000 Da, 11,000 to 12,000 Da, 11,000 to 13,000 Da, 11,000 to 14,000 Da, 11,000 to 15,000 Da, 11,500 to 12,000 Da, 11,500 to 13,000 Da, 11,500 to 14,000 Da, 11,500 to 15,000 Da, 12,000 to 13,000 Da, 12,000 to 14,000 Da, 12,000 to 15,000 Da, 12,500 to 13,000 Da, 12,500 to 14,000 Da, 12,500 to 15,000 Da, 13,000 to 14,000 Da, 13,000 to 15,000 Da, 13,500 to 14,000 Da, 13,500 to 15,000 Da, 14,000 to 15,000 Da, 14,500 to 15,000 Da.

In some embodiments, the sulfated glycosaminoglycan includes no more than 10 wt % of carbohydrates or other contaminants with a molecular weight below 1,000 Daltons. In other embodiments, the sulfated glycosaminoglycan includes no more than 1 wt %, no more than 2 wt %, no more than 3 wt %, no more than 4 wt %, no more than 5 wt %, no more than 6 wt %, no more than 7 wt %, no more than 8 wt %, or no more than 9 wt % of carbohydrates or other contaminants with a molecular weight below 1,000 Daltons.

In some embodiments, the sulfated glycosaminoglycan includes no more than 20 wt % of carbohydrates or other contaminants with a molecular weight below 3,000 Daltons. In other embodiments, the sulfated glycosaminoglycan includes no more than 1 wt %, no more than 2 wt %, no more than 3 wt %, no more than 4 wt %, no more than 5 wt %, no more than 6 wt %, no more than 7 wt %, no more than 8 wt %, or no more than 9 wt %, no more than 10 wt %, no more than 11 wt %, no more than 12 wt %, no more than 13 wt %, no more than 14 wt %, no more than 15 wt %, no more than 16 wt %, no more than 17 wt %, no more than 18 wt %, or no more than 19 wt % of carbohydrates or other contaminants with a molecular weight below 3,000 Daltons.

In some embodiments, the sulfated glycosaminoglycan includes no more than 25 wt % of carbohydrates or other contaminants with a molecular weight below 5,000 Daltons. In other embodiments, the sulfated glycosaminoglycan includes no more than 1 wt %, no more than 2 wt %, no more than 3 wt %, no more than 4 wt %, no more than 5 wt %, no more than 6 wt %, no more than 7 wt %, no more than 8 wt %, or no more than 9 wt %, no more than 10 wt %, no more than 11 wt %, no more than 12 wt %, no more than 13 wt %, no more than 14 wt %, no more than 15 wt %, no more than 16 wt %, no more than 17 wt %, no more than 18 wt %, or no more than 19 wt %, no more than 20 wt %, no more than 21 wt %, no more than 22 wt %, no more than 23 wt %, or no more than 24 wt % of carbohydrates or other contaminants with a molecular weight below 5,000 Daltons.

In some embodiments, the sulfated glycosaminoglycan contains less than 5,000 ppm of acetic acid. In some embodiments the sulfated glycosaminoglycan contains less than 500 ppm, less than 1,000 ppm, less than 1,500 ppm, less than 2,000 ppm, less than 2,500 ppm, less than 3,000 ppm, less than 3,500 ppm, less than 4,000 ppm, or less than 4,500 ppm of acetic acid. In other embodiments, the sulfated glycosaminoglycan contains less than 5,000 ppm of acetic acid after storage at room temperature for at least 12 months following initiation of storage. In some embodiments the sulfated glycosaminoglycan contains less than 500 ppm, less than 1,000 ppm, less than 1,500 ppm, less than 2,000 ppm, less than 2,500 ppm, less than 3,000 ppm, less than 3,500 ppm, less than 4,000 ppm, or less than 4,500 ppm of acetic acid after storage at room temperature for at least 12 months following initiation of storage. In some embodiments, the sulfated glycosaminoglycan contains less than 5,000 ppm of acetic acid for at least 13 months, at least 14 months, at least 15 months, at least 16 months, at least 17 months, at least 18 months, at least 19 months, at least 20 months, at least 21 months, at least 22 months, at least 23 months, or at least 24 months following initiation of storage.

In some embodiments, the sulfated glycosaminoglycan maintains a white or off-white color after storage at room temperature for at least 6 months following initiation of storage. In some embodiments, the sulfated glycosaminoglycan maintains a white or off-white color after storage at room temperature for at least 7 months, at least 8 months, at least 9 months, at least 10 months, at least 11 months, at least 12 months, at least 13 months, at least 14 months, at least 15 months, at least 16 months, at least 17 months, at least 18 months, at least 19 months, at least 20 months, at least 21 months, at least 22 months, at least 23 months, or at least 24 months following initiation of storage.

All cells and numerous macromolecules in nature carry an array of covalently attached sugars (monosaccharides) or sugar chains (oligosaccharides (usually less than a dozen monosaccharides) or polysaccharides (usually more than a dozen monosaccharides)), which are generically referred to as glycans. Sometimes glycans can be freestanding entities. Being on the outer surface of cellular and secreted macromolecules, many glycans can modulate or mediate a variety of events in cell-cell, cell-matrix and cell-molecule interactions critical to the development and function of a complex multicellular organism.

Most cell-surface polysaccharides found in animals belong to a class of glycans known as glycosaminoglycans (GAGs). Glycosaminoglycans are complex polysaccharides that exist both on the cell surface and free within the extracellular matrix, and belong to a highly heterogeneous class of macromolecules. GAGs (formerly called mucopolysaccharides) are linear macromolecules with molecular mass of >15,000 Daltons (Da). These linear polysaccharides contain repeating disaccharide units, which typically comprise an aminosugar residue, that is glucosamine or galactosamine, and a uronic acid residue containing glucuronic acid or iduronic acid. The amino-substituted sugar may be attached to a hexuronic acid residue. Modifications on the sugar residues are common, particularly the sulfation of hydroxyl or amino groups. The sulfates and hexuronic acid carboxylate groups are negatively charged under physiological conditions. The hydroxyl group at $C_2$, $C_3$, $C_4$ and $C_6$ and the amino group on $C_2$ may be substituted by sulfate groups. The GAGs are represented by the following compounds: heparin, heparan sulfate, dermatan sulfate, hyaluronic acid, chondroitin sulfate, and keratan sulfate. These GAGs structurally differ in their disaccharide repeating units (building blocks). These complex carbohydrate macromolecules are found in humans and animals, with several located in the tissues and fluids. GAGs are responsible for performing and regulating a vast number of essential cellular functions, and with regard to soft tissue; they play a key role in promoting healing and/or reducing coagulation. GAGs show biological function primarily through their interactions with the hundreds of GAG-binding proteins found on cellular surfaces and in extracellular spaces. The structural factors that affect the strength and specificity of binding are key to the elicitation of a proper biological response. Glycans have many protective, stabilizing, organizational and barrier functions. Glycosaminoglycans (GAGs) are signaling glycans, because they interact with receptor tyrosine kinases and/or their ligands and facilitate changes in cell behavior.

Chondroitin sulfate is a sulfated GAG composed of a chain of alternating sugars (N-acetylgalactosamine and glucuronic acid), with an average molecular weight of 20,000-30,000 Da. It is derived from numerous species, including mammals and fish. Each monosaccharide may be left unsulfated, sulfated once, or sulfated twice. The most common pattern is that the hydroxyl groups of the 4 and 6 positions of the N-acetyl-galactosamine are sulfated, with some chains having the position 2 of the glucuronic acid sulfated. A chondroitin chain can have over 100 individual sugars, each of which can be sulfated in variable positions and quantities. Chondroitin sulfate is an important structural component of cartilage and provides much of its resistance to compression. Chondroitin sulfate is often mixed with glucosamine in therapeutic agents that are orally administered.

Mucopolysaccharide polysulphate (MPS) is a naturally occurring organoheparinoid compound. MPSs are comprised of long unbranched polysaccharides with repeating disaccharide units. The chemical structure permits considerable hydrogen bonding with adjacent water molecules, which effectively leads to hydration of the surrounding tissue through its water retention property (Pichotka et al., "Experimental Studies on Percutaneous Efficacy of Anticoagulative Substances; Potentiation of Intravenously Administered Heparin by Percutaneous Hirudoid," *Arzneimittel-Forschung* 4(4):277-282 (1954); Buchtela et al., "The Percutaneous Resorption of an S35-labelled Mucopolysaccharide Polysulfuric Acid Ester," *Arzneimittel-Forschung* 17(5):591-593 (1967); and Larsson et al., "Percutaneous Treatment With a Mucopolysaccharide Polysulphate of Experimentally Induced Subcutaneous Haematomas in Man," *Thrombosis and Haemostasis* 53(3):343-345 (1985), which are hereby incorporated by reference in their entirety). MPS has been separately described as a semi-synthetic glycosaminoglycan with a mean molecular mass of 9700 Da with multifold actions.

Polysulfated glycosaminoglycan (PSGA G) is chemically similar to natural mucopolysaccharides found in cartilaginous tissues. It is composed of repeat disaccharide units (comprising hexosamine and hexuronic acid), and since it is similar to GAGs already present in cartilage; PSGAG thus easily integrates itself there (Wanamaker et al., "Applied Pharmacology for Veterinary Technicians—E-Book," Elsevier Health Sciences, p. 392. ISBN 9780323291705 (2014 Mar. 25); and White "Adequan: A Review for the Practicing Veterinarian," *J. Equine Vet. Sci.* 8(6):463-468 (1988), which are hereby incorporated by reference in their entirety). PSGAG is prepared from chondroitin sulfate through a process of extensive sulfation, fragmentation, and purification. Whereas chondroitin sulfate is typically in a molecular weight range of 20,000 to 30,000 Da, PSGAG, in accordance with the present application, is typically prepared in a molecular weight range of 3,000 to 15,000 Da.

The specific mechanism of action of Adequan® in canine joints is not known. PSGAG is characterized as a "disease modifying osteoarthritis drug". Experiments conducted in vitro have shown PSGAG to inhibit certain catabolic enzymes which have increased activity in inflamed joints, and to enhance the activity of some anabolic enzymes. For example, PSGAG has been shown to significantly inhibit serine proteinases. Serine proteinases have been demonstrated to play a role in the Interleukin-1 mediated degradation of cartilage proteoglycans and collagen. PSGAG is reported to be an inhibitor of Prostaglandin E2 (PGE2) synthesis. PGE2 has been shown to increase the loss of proteoglycan from cartilage. PSGAG has been reported to inhibit some catabolic enzymes such as elastase, stromelysin, metalloproteases, cathepsin B 1, and hyaluronidases, which degrade collagen, proteoglycans, and hyaluronic acid in degenerative joint disease. Anabolic effects studied include ability to stimulate the synthesis of protein, collagen, proteoglycans, and hyaluronic acid in various cells and tissues in vitro. Cultured human and rabbit chondrocytes have shown increased synthesis of proteoglycan and hyaluronic acid in the presence of PSGAG. PSGAGs have shown a specific potentiating effect on hyaluronic acid synthesis by synovial membrane cells in vitro.

Absorption, distribution, metabolism, and excretion of PSGAG following intramuscular injection have been studied in several species, including rats, rabbits, humans, horses and dogs.

Studies in rabbits showed maximum blood concentrations of PSGAG following IM injection were reached between 20 to 40 minutes following injection, and that the drug was distributed to all tissues studied, including articular cartilage, synovial fluid, adrenals, thyroid, peritoneal fluid, lungs, eyes, spinal cord, kidneys, brain, liver, spleen, bone marrow, skin, and heart.

Following intramuscular injection of PSGAG in humans, the drug was found to be bound to serum proteins. PSGAG binds to both albumin and chi- and beta-globulins and the extent of the binding is suggested to be 30 to 40%. Therefore, the drug may be present in both bound and free form in the bloodstream. The synovial membrane is not a significant barrier to distribution of PSGAG from the bloodstream to the synovial fluid. Distribution from the synovial fluid to the cartilage takes place by diffusion. In the articular cartilage the drug is deposited into the cartilage matrix.

Serum and synovial fluid distribution curves of PSGAG have been studied in dogs and appear similar to those found in humans and rabbits.

As used herein, "skin," "skin surface," "derma," "epidermis," and similar terms are used interchangeably, and refer not only to the outer skin of a subject comprising the epidermis, but also to underlying layers and to mucosal surfaces. The skin site is intact (e.g., normal skin), as opposed to being compromised (i.e. damaged or that lacking at least some of the stratum corneum (e.g., skin damaged by exposure to the agent in question, radiation exposure, another agent, the presence of a pathological condition such as a rash or contact dermatitis, a physical trauma such as a cut, wound, or abrasion, an underdeveloped skin such as occurs in a preterm infant, conditions in which either all or part of the epidermis is exposed, conditions in which part of the dermis has been removed such as partial thickness wounds encountered in resurfacing procedures such as chemical peels, dermabrasions, and laser resurfacing, etc.)).

For a topical application of an active pharmaceutical ingredient (API) to be effective, the active ingredient needs to penetrate through the stratum corneum (SC), the skin's outermost layer, to reach the lower levels of the epidermis. The barrier function of the skin must be overcome for such transdermal delivery of active ingredients to occur. A common method for permeating the skin barrier is to use additive chemicals that act as penetration enhancers. These chemical penetration enhancers are molecules that increase the permeability of the SC. The effects and mechanisms of several chemical enhancers are summarized in Kim et al., "Transdermal Delivery Systems in Cosmetics," *Biomedl Dermatol.* 4(10):1-12 (2020), which is hereby incorporated by reference in its entirety.

As used herein, "transdermal penetration" refers to administration through the skin. Transdermal administration is often applied where systemic delivery of an active is desired, although it may also be useful for delivering an active to tissues underlying the skin with minimal systemic absorption.

In some embodiments, the skin penetrating agent comprises a penetration enhancer. The term "penetration enhancer" as used herein refers to a chemical substance delivered along with the intended drug, or prior to drug administration, that promotes the transdermal penetration of the drug applied at the surface of the skin. Penetration enhancers have been used to increase the rate at which drugs penetrate the skin. Ideally, such chemical enhancers are passive and innocuous and merely facilitate diffusion of the intended drug through the stratum corneum, whereupon it can diffuse through the extracellular matrix to reach the site of action.

Suitable skin penetration enhancers can be, for example, sulfoxides, alcohols, fatty acids, esters of saturated or unsaturated fatty acids, polyols, amides, surfactants, terpenes and terpenoids, alkanones, organic acids and esters, cyclodextrins, water, vitamin E, phospholipids, essential oils and their terpene components, vegetable carrier oils, isoforms of alcohols, aliphatic diols and triols, urea or other amide derivatives, tocopherol acetate, aloe derivatives, silicon derivatives, chelating agents, water, emulsifiers, polyoxy ethers of fatty acids, vitamins, antioxidants, antimicrobial preservatives, and combinations thereof. To date, more than 350 chemicals have been demonstrated to enhance skin permeability (Karande et al., "Discovery of Transdermal Penetration Enhancers by High-throughput Screening," *Nat Biotechnol.* 22:192-197 (2004), which is hereby incorporated by reference in its entirety), including terpenes, sulfoxides, laurocapram, pyrrolidones, fatty acids, fatty alcohols, alcohols such as glycol, surfactants, and urea (Chen et al., "Novel Chemical Permeation Enhancers for Transdermal Drug Delivery," *Asian J Pharm Sci.* 9(2):51-64 (2014), which is hereby incorporated by reference in its entirety). Urea has long been used in topical and transdermal preparations and is variously described for its moisturizing, keratolytic and penetration-enhancing activities.

In some embodiments, the skin penetrating agent is selected from the group consisting of acetone, acyl lactylates, acyl peptides, acylsarcosinates, alkanolamine salts of fatty acids, alkyl benzene sulphonates, alkyl ether sulphates, alkyl sulphates, anionic surface-active agents, benzyl benzoate, benzyl salicylate, butan-1,4-diol, butyl benzoate, butyl laurate, butyl myristate, butyl stearate, cationic surface-active agents, citric acid, cocoamidopropylbetaine, decyl methyl sulfoxide, decyl oleate, dibutyl azelate, dibutyl phthalate, dibenzyl sebacate, dibutyl sebacate, dibutyl suberate, dibutyl succinate, dicapryl adipate, didecyl phthalate, diethylene glycol, diethyl sebacate, diethyl-m-toluamide, di(2-hydroxypropyl)ether, diisopropyl adipate, diisopropyl sebacate, N,N-dimethyl acetamide, dimethyl azelate, N,N-dimethyl formamide, 1,5-dimethyl-2-pyrrolidone, dimethyl sebacate, dimethyl sulfoxide, dioctyl adipate, dioctyl azelate, dioctyl sebacate, 1,4 dioxane, 1-dodecylazacyloheptan-2-one, dodecyl dimethyl amine oxides, ethyl caprate, ethyl caproate, ethyl caprylate, 2-ethyl-hexyl pelargonate, ethyl-2-hydroxypropanoate, ethyl laurate, ethyl myristate, 1-ethyl-2-pyrrolidone, ethyl salicylate, hexyllaurate, 2-hydroxyoc-tanoic acid, 2-hydroxypropanoic acid, 2-hydroxypropionic acid, isothionates, isopropyl isostearate, isopropyl palmitate, guar hydroxypropyltrimonium chloride, hexan-2,5-diol, khellin, lamepons, lauryl alcohol, maypons, metal salts of fatty acids, methyl nicotinate, 2-methylpropan-2-ol, 1-methyl-2-pyrrolidone, 5-methyl-2-pyrrolidone, methyl taurides, miranol surfactants, nonionic surface-active agents, octyl alcohol, octylphenoxy polyethoxyethanol, oleic acid, ethanolamide, oleyl alcohol, pentan-2,4-diol, phenoxyethanol, phosphatidyl choline, phosphine oxides, polyalkoxylated ether glycollates, poly(diallylpiperidinium chloride), poly(dipropyldiallyl ammonium chloride), polyglycerol esters, polyoxyethylene lauryl ether, polyoxy: polyoxyethylene stearate, polyoxypropylene 15 Stearyl ether, poly(vinyl pyridinium chloride), propan-1-ol, propan-2-ol, propylene glycol dipelargonate, pyroglutamic acids, 2-pyrrolidone, pyruvic acids, Quaternium 5, Quaternium 18, Quaternium 19, Quaternium 23, Quaternium 31, Quaternium 40, Quaternium 57, quartenary amine salts, quaternized poly (dimethylaminoethylmethacrylate), quaternized poly(vinyl alcohol), Sapamin hydrochloride, sodium cocaminopropionate, sodium dioctyl sulfosuccinate, sodium laurate, sodium lauryl ether sulfate, sodium lauryl sulfate, sugar esters, sulphosuccinate, tetrahydrofuran, tetrahydro-furfural alcohol, transcutol, triethanolamine dodecyl ben-zene sulphonate, triethanolamine oleate, water and deriva-tives, salts, essential oils and their terpene components, vegetable carrier oils, emulsifiers, ethanol, dimethyl sulfox-ide, dimethyl isosorbide, isopropyl myristate, propylene glycol, sodium lauryl sulfate, lauryl amine oxide, vitamin E, lower alcohols, iso-forms of alcohols, aliphatic diols and triols, urea or other amide derivatives, primary and second-ary alcohols, fatty acids, fatty acid esters, polyols, amides, surfactants, terpenes and terpenoids, alkanones, organic acids and esters, cyclodextrins, phospholipids, and combi-nations thereof.

Among the essential oils are eucalyptus oil, eucalyptol, clove oil, turpentine oil, and peppermint oil. Vegetable carrier oils are natural fixed oils pressed mainly from the seeds and constitute a common constituent of pharmaceuti-cal formulations used topically. They are a mixture of heterogeneous lipids composed mainly of triglycerides, and a lower concentration of components such as free fatty acid (saturated and unsaturated), mono and diglycerides, sterol, phosphatides, fatty alcohol, and lipid-soluble vitamins.

Suitable alcohols include alkanols such as ethanol, pro-panol, butanol, pentanol, hexanol, octanol, n-octanol, nona-nol, decanol, 2-butanol, 2-pentanol, and benzyl alcohol; fatty alcohols, such as caprylic alcohol, decyl alcohol, lauryl alcohol, 2-lauryl alcohol, myristyl alcohol, cetyl alcohol, stearyl alcohol, oleyl alcohol, and linolenyl alcohol; isopro-pyl alcohol, and 2-(2-ethoxy) ethanol.

Examples of suitable fatty acids include linear fatty acids such as valeric acid, heptanoic acid, pelagonic acid, caproic acid, capric acid, lauric acid, myristic acid, stearic acid, oleic acid, linoleic acid, and caprylic acid; and branched fatty acids, such as isovaleric acid, neopentanoic acid, neohep-tanoic acid, neononanoic acid, trimethyl hexanoic acid, neodecanoic acid, and isostearic acid.

Examples of suitable fatty acid esters include aliphatic fatty acid esters such as isopropyl n-butyrate, isopropyl n-hexanoate, isopropyl n-decanoate, isopropyl myristate, isopropyl palmitate, and octyldodecyl myristate; alkyl fatty acid esters such as ethyl acetate, butyl acetate, methyl acetate, methylvalerate, methylpropionate, diethyl sebacate, and ethyl oleate, and diisopropyl adipate.

Examples of suitable polyols include propylene glycol, propylene glycol monolaurate, butylene glycol, polyethyl-ene glycol, ethylene glycol, diethylene glycol, triethylene glycol, dipropylene glycol, ethoxydiglycol, pentylene gly-col, glycerol, propanediol, butanediol, pentanediol, hexan-etriol, and glycerin.

Examples of suitable amides include urea, dimethylacet-amide, diethyltoluamide, dimethylformamide (DMF), dim-ethyloctamide, dimethyldecamide, biodegradable cyclic urea (e.g., 1-alkyl-4-imidazoline-2-one), pyrrolidone deriva-tives, biodegradable pyrrolidone derivatives (e.g., fatty acid esters of N-(2-hydroxyethyl)-2-pyrrolidone), cyclic amides, hexamethylenelauramide and its derivatives, dietha-nolamine, and triethanolamine. Examples of pyrrolidone derivatives include 1-methyl-2-pyrrolidone, N-methyl-2-pyrrolidone, 2-pyrrolidone, 1-lauryl-2-pyrrolidone, 1-methyl-4-carboxy-2-pyrrolidone, 2-pyrrolidone-5-carbox-ylic acid, 1-hexyl-4-carboxy-2-pyrrolidone, 1-lauryl-4-car-boxy-2-pyrrolidone, 1-methyl-4-methoxycarbonyl-2-pyr-rolidone, 1-hexyl-4-methoxycarbonyl-2-pyrrolidone, 1-lauryl-4-methoxycarbonyl-2-pyrrolidone, N-cyclohex-ylpyrrolidone, N-dimethylaminopropylpyrrolidone, N-co-coalkypyrrolidone, N-tallowalkylpyrrolidone, and N-meth-ylpyrrolidone. Examples of cyclic amides include 1-dodecylazacycloheptane-2-one (e.g., Azone™ (e.g., Syn-tec Pharma Corp, Farmingdale, N.Y.)), 1-geranylazacyclo-heptan-2-one, 1-farnesylazacycloheptan-2-one, 1-gera-nylgeranylazacycloheptan-2-one, 1-(3,7-dimethyloctyl) azacycloheptan-2-one, 1-(3,7,11-trimethyldodecyl) azacyclohaptane-2-one, 1-geranylazacyclohexane-2-one, 1-geranylazacyclopentan-2,5-dione, and 1-farnesylazacy-clopentan-2-one.

Suitable surfactants include anionic surfactants such as sodium laurate, sodium lauryl sulfate, among others; cat-ionic surfactants such as benzalkonium chloride, dodecylt-rimethylammonium chloride, cetyltrimethylammonium bro-mide; non-ionic surfactants such as the propoxylated polyoxyethylene ethers, e.g., Poloxamer 231, Poloxamer 182, Poloxamer 184, polyoxyethylene esters, sorbitan mono-9-octadecenoate, the ethoxylated fatty acids, e.g., Tween 20, Myrj 45, the sorbitan derivatives, e.g., Tween 40, Tween 60, Tween 80, Span 60, the ethoxylated alcohols, e.g., polyoxyethylene (4) lauryl ether (Brij® 30), polyoxyethyl-ene (2) oleyl ether, caprylocaproyl polyoxyl-8 glyceride, polyglyceryl oleate, polyoxyethylated glycolysed glycer-ides, polysorbates, monoglycerides, lecithin, and lecithin derivatives.

Suitable terpenes and terpenoids include D-limonene, opinene, β-carene, oterpineol, carvol, carvone, menthone, limonene oxide, opinene oxide, eucalyptus oil, terpineol, and menthol.

Examples of suitable organic acids and esters include salicyclic acid, methyl salicylate, citric acid, lauryl lactate, and succinic acid.

Other examples of suitable penetration enhancers include glycerol monoethyl ether, β-cyclodextrin, and polyglycosy-lated glycerides.

In some embodiments, the skin penetration enhancer is one or more of Laurogicol™ 90, Transcutol® (diethylene glycol monoethyl ether) (Gattefossé Corporation, Paramus, N.J.), Labrasol® (PEG-8 caprylic/capric glycerides) (Gat-tefossé Corporation, Paramus, N.J.), VersaBase®, Plurol® Oleique (Polyglyceryl-3 oleate) (Gattefossé Corporation, Paramus, N.J.), Labrafil® 2125cs (Gattefossé Corporation, Paramus, N.J.), oleic acid, HPbCD, Pentravan® (Fagron, Inc., St. Paul, Minn.), Pentravan® Plus (Fagron, Inc., St. Paul, Minn.), Phytobase™ (Fagron, Inc., St. Paul, Minn.), Lipovan® (Fagron, Inc., St. Paul, Minn.) and Pluronic Lecithin Organogel (PLO), Humco HRT Heavy™ and HRT Botanical™ (Humco, Texarkana, Tex.), Fagron HRT Heavy™ (Fagron, Inc., St. Paul, Minn.), Fagron HRT Botanical™ (Fagron, Inc., St. Paul, Minn.), Letco HRT Cream (Letco Medical, Decatur, Ala.), Medisca PenDerm™ (Medisca Inc., Plattsburgh, NY), Azone® (1-dodecylazacy-cloheptan-2-one), CPE-215® (Cyclopentadecalactone), NexAct® (Alkyl-2-(N,N-disubstituted amino)-alkanoate ester), DEPA® (2-(n-nonyl)-1,3-dioxolane), LIPODERM® (Professional Compounding Centers of America, Inc., Houston, Tex.), Humco Salt Stable, Medisca Salt Stable, etc., lecithin isopropyl palmitate (LIPS), and penetration enhancers shown for example in U.S. Pat. Nos. 3,909,816; 4,405, 616; 4,801,586; 4,861,764; 4,886,783; 4,983,396; 5,118, 845; and 5,196,410, each of which is hereby expressly incorporated herein by reference in its entirety.

LIPODERM® reportedly comprises ethoxydiglycol, water, glycerin, C12-C15 alkyl benzoate, glyceryl stearate, dimethicone, cetearyl alcohol, cetearyl glucoside, polyacrylamide, cetyl alcohol, magnesium aluminum silicate, xanthan gum, aloe vera, tocopheryl acetate, bitter almond kernel oil, grape seed extract, wheat germ oil, vitamin-A palmitate, vitamin-C palmitate, ProLipo mutli-emulsion liposomic system, tetrasodium EDTA, phenoxyethanol, and sodium hydroxymethyl glycinate.

Pentravan®, having fatty acid alcohols, acids, esters, phospholipids, antioxidants, skin-feel enhancer, natural humectant, natural preservatives, nonionic emulsifiers, anionic emulsifiers, and buffer, is a transdermal penetrating functional bioactive oil-in-water emulsion with a phospholipid matrix and pharmacologically accepted actives. Pentravan® gel is an emollient which softens and moisturizes the skin. Emollients may be used as lubricants to treat or prevent dry, itchy skin and minor skin irritations. The skin penetrating topical composition may also be a formulation comprised of approximately 80% by weight pleurinic gel and approximately 20% by weight lipoil.

The commercially available carriers listed above represent effective skin penetrating enhancers; however, one skilled in the art will recognize that topical carriers meeting the specific chemical requirements of an individual drug can be formulated for maximum efficiency in topical delivery. Rather than using commercially available bases such as these, ingredients similar to those found in these bases may be used to form new bases that can be used in the therapeutic compositions herein. For example, other fatty alcohols, oils, lipids, gums, polymers, and the like, may be compounded to produce therapeutic compositions within the scope of the present disclosure.

In some cases, the skin penetration enhancer also functions as a solvent. For example, the formulations of the present disclosure may include a solvent, such as water, purified water, hexylene glycol, propylene glycol, oleyl alcohol, propylene carbonate, dimethylsulfoxide, N-methylpyrrolidone, and mineral oil. Sometimes, the solvent also functions as a skin penetration enhancer. In other cases, the solvent does not function as a skin penetration enhancer.

In some embodiments, the carrier is selected from the group consisting of a transdermal tape, a transdermal patch, an ointment, a cream, a gel, a paste, a collodion composition, a foam, a rapid dissolving solid, and a lotion. As used herein, "carrier," and "pharmaceutical carrier" may be used interchangeably, and refer to any liquid, gel, salve, solvent, liquid, diluent, fluid ointment base, liposome, micelle, giant micelle, and the like, which is suitable for use in contact with a subject or its tissue without causing adverse physiological responses, and which does not interact with the other components of the composition in a deleterious manner. A number of carrier ingredients are known for use in making topical formulations, such as gelatin, polymers, fats and oils, lecithin, collagens, alcohols, water, etc.

In some embodiments, the pharmaceutical composition further comprises a pharmaceutically active agent selected from the group consisting of pharmaceutically acceptable free bases, salts, esters, ethers, or solvates of antibiotics, anti-infectives, antimycotics agents, steroids, cannabinoids, antihistamines, anti-inflammatory agents, antiparasitic agents, immunomodulators, antisense agents, antiviral agents, treatments for hyper- and hypo skin pigmentation disorders, anti-psoriatic agents, keratolytic agents, DNA synthesis inhibitors, cytotoxic agents, antithyroid agents, monoclonal antibody regulators, TNF alpha antagonists, immunoglobulins, metabolic regulators, antiangiogenic agents, protease inhibitors, anxiolytics, kinase regulators, cell growth regulators, enzymes, prostaglandins, peptides, analgesics, skin moisturizers, astringents, exfoliating agents, agents intended to protect the skin or modify its appearance or improve its rate of healing, and combinations thereof.

In some embodiments, the pharmaceutical composition further comprises an additive selected from the group consisting of adjuvants, gelling agents, thickeners, solvents, preservatives, pH modifiers, colorants, perfumes, flavors, propellants, absorbents, adsorbents, antioxidants, antimicrobial preservatives, and/or combinations thereof. In some embodiments the additive is selected from the group consisting of tocopherol acetate, an aloe derivative, a silicon derivative, a chelating agent, an emulsifier, a polyol, water, and combinations thereof.

The gelling agent may be selected from the group consisting of hydroxyethyl cellulose, hyaluronic acid, Natrasol, pectines, agar, alginic acid and its salts, guar gum, pectin, polyvinyl alcohol, polyethylene oxide, cellulose and its derivatives, propylene carbonate, polyethylene glycol, hexylene glycol sodium carboxymethylcellulose, polyacrylates, polyoxyethylene-polyoxypropylene block copolymers, pluronics, wood wax alcohols, and tyloxapol.

In some embodiments, the composition comprises 0.1 to 25 wt % of the sulfated glycosaminoglycan, 20 to 60 wt % of the skin penetrating agent, and 20 to 80 wt % of the carrier and gelling/thickening agent. For example, in some embodiments, the sulfated glycosaminoglycan is present in the formulation in an amount ranging from about 0.1 wt % to 1 wt %, 0.1 wt % to 5 wt %, 0.1 wt % to 10 wt %, 0.1 wt % to 15 wt %, 0.1 wt % to 20 wt %, 0.1 wt % to 25 wt %, 0.5 wt % to 1 wt %, 0.5 wt % to 5 wt %, 0.5 wt % to 10 wt %, 0.5 wt % to 15 wt %, 0.5 wt % to 20 wt %, 0.5 wt % to 25 wt %, 1 wt % to 5 wt %, 1 wt % to 10 wt %, 1 wt % to 15 wt %, 1 wt % to 20 wt %, 1 wt % to 25 wt %, 5 wt % to 10 wt %, 5 wt % to 15 wt %, 5 wt % to 20 wt %, 5 wt % to 25 wt %, 10 wt % to 15 wt %, 10 wt % to 20 wt %, 10 wt % to 25 wt %, 15 wt % to 20 wt %, 15 wt % to 25 wt %, 20 wt % to 25 wt %, based on weight of the composition. In some embodiments, the skin penetrating agent is present in the formulation in an amount ranging from about 20 wt % to 30 wt %, 20 wt % to 40 wt %, 20 wt % to 50 wt %, 20 wt % to 60 wt %, 25 wt % to 30 wt %, 25 wt % to 40 wt %, 25 wt % to 50 wt %, 25 wt % to 60 wt %, 30 wt % to 40 wt %, 30 wt % to 50 wt %, 30 wt % to 60 wt %, 35 wt % to 40 wt %, 35 wt % to 50 wt %, 35 wt % to 60 wt %, 40 wt % to 50 wt %, 40 wt % to 60 wt %, 45 wt % to 50 wt %, 45 wt % to 60 wt %, 50 wt % to 60 wt %, 55 wt % to 60 wt % based on weight of the composition. In some embodiments, the carrier is present in the formulation in an amount ranging from about 20 wt % to 30 wt %, 20 wt % to 40 wt %, 20 wt % to 50 wt %, 20 wt % to 60 wt %, 20 wt % to 70 wt %, 20 wt % to 80 wt %, 30 wt % to 40 wt %, 30 wt % to 50 wt %, 30 wt % to 60 wt %, 30 wt % to 70 wt %, 30 wt % to 80 wt %, 40 wt % to 50 wt %, 40 wt % to 60 wt %, 40 wt % to 70 wt %, 40 wt % to 80 wt %, 50 wt % to 60 wt %, 50 wt % to 70 wt %, 50 wt % to 80 wt %, 60 wt % to 70 wt %, 60 wt % to 80 wt %, 70 wt % to 80 wt % based on weight of the composition.

In some embodiments, the composition comprises 5 to 16 wt % of the sulfated glycosaminoglycan, 25 to 55 wt % of the skin penetrating agent, and 25 to 75 wt % of the carrier. For example, in some embodiments, the sulfated glycosaminoglycan is present in the formulation in an amount ranging from about 5 wt % to 6 wt %, 5 wt % to 7 wt %, 5 wt % to 8 wt %, 5 wt % to 9 wt %, 5 wt % to 10 wt %, 5 wt % to 11 wt %, 5 wt % to 12 wt %, 5 wt % to 13 wt %, 5 wt % to 14 wt %, 5 wt % to 15 wt %, 5 wt % to 16 wt %, 7 wt % to 8 wt %, 7 wt % to 9 wt %, 7 wt % to 10 wt %, 7 wt % to 11 wt %, 7 wt % to 12 wt %, 7 wt % to 13 wt %, 7 wt % to 14 wt %, 7 wt % to 15 wt %, 7 wt % to 16 wt %, 9 wt % to 10 wt %, 9 wt % to 11 wt %, 9 wt % to 12 wt %, 9 wt % to 13 wt %, 9 wt % to 14 wt %, 9 wt % to 15 wt %, 9 wt % to 16 wt %, 11 wt % to 12 wt %, 11 wt % to 13 wt %, 11 wt % to 14 wt %, 11 wt % to 15 wt %, 11 wt % to 16 wt %, 13 wt % to 14 wt %, 13 wt % to 15 wt %, 13 wt % to 16 wt %, 14 wt % to 16 wt %, 14 wt % to 15 wt %, 15 wt % to 16 wt % based on weight of the composition. In some embodiments, the skin penetrating agent is present in the formulation in an amount ranging from about 25 wt % to 30 wt %, 25 wt % to 35 wt %, 25 wt % to 40 wt %, 25 wt % to 45 wt %, 25 wt % to 50 wt %, 25 wt % to 55 wt %, 30 wt % to 35 wt %, 30 wt % to 40 wt %, 30 wt % to 45 wt %, 30 wt % to 50 wt %, 30 wt % to 55 wt %, 35 wt % to 40 wt %, 35 wt % to 45 wt %, 35 wt % to 50 wt %, 35 wt % to 55 wt %, 40 wt % to 45 wt %, 40 wt % to 50 wt %, 40 wt % to 55 wt %, 45 wt % to 50 wt %, 45 wt % to 55 wt %, 50 wt % to 55 wt % based on weight of the composition. In some embodiments, the carrier is present in the formulation in an amount ranging from about 25 wt % to 30 wt %, 25 wt % to 35 wt %, 25 wt % to 40 wt %, 25 wt % to 45 wt %, 25 wt % to 50 wt %, 25 wt % to 55 wt %, 25 wt % to 60 wt %, 25 wt % to 65 wt %, 25 wt % to 70 wt %, 25 wt % to 75 wt %, 30 wt % to 35 wt %, 30 wt % to 40 wt %, 30 wt % to 45 wt %, 30 wt % to 50 wt %, 30 wt % to 55 wt %, 30 wt % to 60 wt %, 30 wt % to 65 wt %, 30 wt % to 70 wt %, 30 wt % to 75 wt %, 35 wt % to 40 wt %, 35 wt % to 45 wt %, 35 wt % to 50 wt %, 35 wt % to 55 wt %, 35 wt % to 60 wt %, 35 wt % to 65 wt %, 35 wt % to 70 wt %, 35 wt % to 75 wt %, 40 wt % to 45 wt %, 40 wt % to 50 wt %, 40 wt % to 55 wt %, 40 wt % to 60 wt %, 40 wt % to 65 wt %, 40 wt % to 70 wt %, 40 wt % to 75 wt %, 45 wt % to 50 wt %, 45 wt % to 55 wt %, 45 wt % to 60 wt %, 45 wt % to 65 wt %, 45 wt % to 70 wt %, 45 wt % to 75 wt %, 50 wt % to 55 wt %, 50 wt % to 60 wt %, 50 wt % to 65 wt %, 50 wt % to 70 wt %, 50 wt % to 75 wt %, 55 wt % to 60 wt %, 55 wt % to 65 wt %, 55 wt % to 70 wt %, 55 wt % to 75 wt %, 60 wt % to 65 wt %, 60 wt % to 70 wt %, 60 wt % to 75 wt %, 65 wt % to 70 wt %, 65 wt % to 75 wt %, 70 wt % to 75 wt % based on weight of the composition.

Another aspect of the present application relates to a method of treating a subject for pain, joint stiffness, soft tissue injury, connective tissue disorders, and/or muscle soreness by administering a pharmaceutical composition of the present disclosure. This method comprises selecting a subject in need of treatment for pain, joint stiffness, soft tissue injury, connective tissue disorders, and/or muscle soreness; administering to the selected subject a storage stable pharmaceutical composition comprising a sulfated glycosaminoglycan having an average molecular weight ranging from 3,000 to 15,000 Daltons, a skin penetrating agent, where the skin penetrating agent promotes transdermal penetration of said sulfated glycosaminoglycan when applied to intact skin surfaces, and a pharmaceutical carrier for topical application, where the pharmaceutical carrier is mixed with the sulfated glycosaminoglycan and the skin penetrating agent. The administering is carried out topically at a location proximate to where the subject is experiencing pain, joint stiffness, soft tissue injury, connective tissue disorders, and/or muscle soreness.

Suitable pharmaceutical compositions are those of the present disclosure as described herein.

The terms "treat", "treatment of", "treating" and the like refer to both therapeutic treatment and prophylactic or preventative measures, wherein the object is to protect against (partially or wholly) or slow down (for example, lessen or postpone the onset of) an undesired physiological condition, disorder or disease, or to obtain beneficial or desired clinical results such as partial or total restoration or inhibition in decline of a parameter, value, function or result that had or would become abnormal. For example, beneficial or desired clinical results include, but are not limited to, alleviation of symptoms; diminishment of the extent or vigor or rate of development of the condition, disorder or disease; stabilization (i.e., not worsening) of the state of the condition, disorder or disease; delay in onset or slowing of the progression of the condition, disorder or disease; amelioration of the condition, disorder or disease state; and remission (whether partial or total), whether or not it translates to immediate lessening of actual clinical symptoms, or enhancement or improvement of the condition, disorder or disease. Treatment seeks to elicit a clinically significant response without excessive levels of side effects.

In some embodiments, the selected subject is treated for pain. Pain sensations include sharp pain, dull pain, ache, and other forms of pain sensations. Pain is a sensation that may be of varying intensity and duration, and may result from a variety of causes. For example, pain may be acute, e.g., as a result of injury, illness or trauma; may be chronic, e.g., as a result of a chronic disease or condition, inflammation, cancer, or other cause; may be localized or diffuse; and may be of low intensity, moderate intensity, or high intensity. Thus, pain is a varied sensation, which includes, for example, acute pain, chronic pain, visceral pain, surgical pain, joint pain, bone pain, back pain, headache pain, neurogenic pain, phantom-limb pain, and other forms and experiences of pain.

In some embodiments, the selected subject is treated for joint stiffness. A joint is formed where two bones meet. The healthy joint bones are lined with spongy cartilage which act as shock absorbers, and the synovial fluid, which is secreted by the synovial membrane lining the joint space, acts as a lubricant that prevents friction. Joint function can be measured by evaluating parameters such as the range of motion and presence of discomfort or pain during movement. Common disorders of the joint include osteoarthritis, rheumatoid arthritis, gout, lupus, tendonitis, bursitis, carpal tunnel syndrome, sprains, etc.

In some embodiments, the selected subject is treated for osteoarthritic pain. Osteoarthritis (OA) is a condition which occurs due to the progressive degeneration and the wearing away of the cartilage (the cushion between the joints), especially at the large joints like the hips and knees. It is a normal age-related degenerative process, occurring gradually after normal wear and tear. OA begins with the breakdown of cartilage resulting in pain, inflammation, and progressive stiffness in the joint.

Osteoarthritic pain can have one or both of an inflammatory and a non-inflammatory component. Non-inflammatory osteoarthritic pain is a specific type of non-inflammatory musculoskeletal pain which typically arises from effects of osteoarthritis-related morphological alterations, such as cartilage degradation, bone changes on sensory neurons, and vascularization of bone remodeling. It is often characterized as a deep, aching sensation that intensifies with motion. It is usually intermittent and often mild, but can become persistent and severe. Crepitus is usually noted in the affected joints. Inflammatory osteoarthritic pain typically occurs from synovial inflammation following pathological processes in cartilage and bone involving tissue damage and macrophage infiltration (resulting in edema) associated with a classical immune system response. The pharmaceutical composition of the present disclosure is particularly suited for relieving joint pain associated with osteoarthritis when the pain relief composition is applied to the subject's knee, hip, elbow, shoulder, wrist, ankle, back, knuckle or other joints that are exhibiting pain and stiffness due to OA.

In some embodiments, the selected subject is treated for soft tissue injury. Soft tissue injury can result from a sport-induced injury, such as a sprain, tennis elbow, or runner's knee, and refers to chronic and acute damage of soft tissues, including muscles, ligaments, tendons, tendon sheath, and cartilage. Ligaments are bands of tissue that connect bones. Tendons are bands of tissue that connect muscle to bone. The tendon sheath is the tissue that surrounds and lubricates the tendon. Injury to any of these soft tissues can produce inflammation, pain, and stiffness.

In some embodiments, the selected subject is treated for muscle soreness.

In some embodiments, the selected subject is treated for connective tissue disorders. Connective tissue is made up of two proteins, collagen and elastin. Collagen is found in the tendons, ligaments, skin, cornea, cartilage, bone and blood vessels; and elastin is the major component of ligaments and skin. A connective tissue disorder results when these connective tissues become inflamed. There are over 200 disorders that impact connective tissue. They may be inherited, caused by environmental factors, or most often, are of unknown cause. Connective tissue diseases include, but are not limited to rheumatoid arthritis, scleroderma, granulomatosis with polyangiitis, Churg-Strauss syndrome, Ehlers-Danlos syndrome, lupus, microscopic polyangiitis, polymyositis/dermatomyositis, Marfan syndrome, mixed connective tissue disease, undifferentiated connective tissue disease. Body parts that can be affected include bones, joints, skin, heart and blood vessels, and lungs, and symptoms can vary depending on the affected area.

"Subjects" (or "patients") to be treated with the method and composition disclosed herein comprise both human subjects and animal subjects (e.g., dogs, cats, horses, monkeys, etc.) for veterinary purposes. In some embodiments, the selected subject is a mammal. In some embodiments, the selected subject is a human.

Another aspect of the present application relates to a storage stable sulfated glycosaminoglycan having an average molecular weight ranging from 3,000 to 15,000 Daltons. The storage stable sulfated glycosaminoglycan is that of the present disclosure as described herein.

Another aspect of the present application relates to a storage stable pharmaceutical composition comprising a sulfated glycosaminoglycan having an average molecular weight ranging from 3,000 to 15,000 Daltons, and a pharmaceutical carrier, where the pharmaceutical carrier is mixed with the sulfated glycosaminoglycan.

Suitable pharmaceutical compositions are those of the present disclosure as described herein.

In some embodiments, the pharmaceutical carrier is an injectable liquid, solution, or emulsion capable of dissolving said purified sulfated glycosaminoglycan.

In some embodiments, the composition comprises 0.1 to 25 wt % of the sulfated glycosaminoglycan and 75 to 99 wt % of the carrier. For example, in some embodiments, the sulfated glycosaminoglycan is present in the formulation in an amount ranging from about 0.1 wt % to 1 wt %, 0.1 wt % to 5 wt %, 0.1 wt % to 10 wt %, 0.1 wt % to 15 wt %, 0.1 wt % to 20 wt %, 0.1 wt % to 25 wt %, 0.5 wt % to 1 wt %, 0.5 wt % to 5 wt %, 0.5 wt % to 10 wt %, 0.5 wt % to 15 wt %, 0.5 wt % to 20 wt %, 0.5 wt % to 25 wt %, 1 wt % to 5 wt %, 1 wt % to 10 wt %, 1 wt % to 15 wt %, 1 wt % to 20 wt %, 1 wt % to 25 wt %, 5 wt % to 10 wt %, 5 wt % to 15 wt %, 5 wt % to 20 wt %, 5 wt % to 25 wt %, 10 wt % to 15 wt %, 10 wt % to 20 wt %, 10 wt % to 25 wt %, 15 wt % to 20 wt %, 15 wt % to 25 wt %, 20 wt % to 25 wt %, based on weight of the composition. In some embodiments, the carrier is present in the formulation in an amount ranging from about 75 wt % to 80 wt %, 75 wt % to 85 wt %, 75 wt % to 90 wt %, 75 wt % to 95 wt %, 75 wt % to 99 wt %, 80 wt % to 85 wt %, 80 wt % to 90 wt %, 80 wt % to 95 wt %, 80 wt % to 99 wt %, 85 wt % to 90 wt %, 85 wt % to 95 wt %, 85 wt % to 99 wt %, 90 wt % to 95 wt %, 90 wt % to 99 wt %, or 95 wt % to 99 wt % based on weight of the composition.

In some embodiments, the composition comprises 5 to 16 wt % of the sulfated glycosaminoglycan and 84 to 95 wt % of the carrier. For example, in some embodiments, the sulfated glycosaminoglycan is present in the formulation in an amount ranging from about 5 wt % to 6 wt %, 5 wt % to 7 wt %, 5 wt % to 8 wt %, 5 wt % to 9 wt %, 5 wt % to 10 wt %, 5 wt % to 11 wt %, 5 wt % to 12 wt %, 5 wt % to 13 wt %, 5 wt % to 14 wt %, 5 wt % to 15 wt %, 5 wt % to 16 wt %, 7 wt % to 8 wt %, 7 wt % to 9 wt %, 7 wt % to 10 wt %, 7 wt % to 11 wt %, 7 wt % to 12 wt %, 7 wt % to 13 wt %, 7 wt % to 14 wt %, 7 wt % to 15 wt %, 7 wt % to 16 wt %, 9 wt % to 10 wt %, 9 wt % to 11 wt %, 9 wt % to 12 wt %, 9 wt % to 13 wt %, 9 wt % to 14 wt %, 9 wt % to 15 wt %, 9 wt % to 16 wt %, 11 wt % to 12 wt %, 11 wt % to 13 wt %, 11 wt % to 14 wt %, 11 wt % to 15 wt %, 11 wt % to 16 wt %, 13 wt % to 14 wt %, 13 wt % to 15 wt %, 13 wt % to 16 wt %, 14 wt % to 16 wt %, 14 wt % to 15 wt %, 15 wt % to 16 wt % based on weight of the composition. In some embodiments, the carrier is present in the formulation in an amount ranging from about 84 wt % to 90 wt %, 84 wt % to 91 wt %, 84 wt % to 92 wt %, 84 wt % to 93 wt %, 84 wt % to 94 wt %, 84 wt % to 95 wt %, 86 wt % to 90 wt %, 86 wt % to 91 wt %, 86 wt % to 92 wt %, 86 wt % to 93 wt %, 86 wt % to 94 wt %, 86 wt % to 95 wt %, 88 wt % to 91 wt %, 88 wt % to 92 wt %, 88 wt % to 93 wt %, 88 wt % to 94 wt %, 88 wt % to 95 wt %, 90 wt % to 91 wt %, 90 wt % to 92 wt %, 90 wt % to 93 wt %, 90 wt % to 94 wt %, or 90 wt % to 95 wt % based on weight of the composition.

Another aspect of the present application relates to a method of treating a subject for a medically observable improvement. The method comprises selecting a subject in need of treatment for a medically diagnosable condition and administering to the selected subject a storage stable pharmaceutical composition comprising a sulfated glycosaminoglycan having an average molecular weight ranging from 3,000 to 15,000 Daltons and a pharmaceutical carrier to facilitate treatment, where the pharmaceutical carrier is mixed with the sulfated glycosaminoglycan.

Suitable pharmaceutical compositions are those of the present disclosure as described herein.

In some embodiments, the subject is treated for pain, joint stiffness, soft tissue injury, connective tissue disorders, and/or muscle soreness.

Suitable subjects are those of the present disclosure as described herein.

Pain, joint stiffness, soft tissue injury, connective tissue disorders, and/or muscle soreness are those of the present disclosure as described herein.

In some embodiments, the administering is aurol, oral, ophthalmic, nasal, rectal, urethral, vaginal, parenteral (including subcutaneous, intradermal, intramuscular, intravenous, and intraarticular), rectal and topical (including dermal, buccal, sublingual, and intraocular), and/or combinations thereof. The most suitable route may depend upon the condition and disorder of the recipient.

Treatment can be continued for as long or as short a period as desired. The compositions may be administered on a regimen of, for example, one to four or more times per day. A suitable treatment period can be, for example, at least about one week, at least about two weeks, at least about one month, at least about six months, at least about 1 year, or indefinitely. A treatment period can terminate when a desired result, for example a partial or total alleviation of symptoms, is achieved.

In some embodiments, the storage stable pharmaceutical composition is in the form of an aerosol, a chewable bar, a bead, a capsule, a cellular sheet, a chewable gel, a cloth, a concentrate, a cream, a crystal, a disc, a douche, a dressing, a drug-eluting contact lens, an elixir, an emulsion, an enema, an extract, an extended release fiber, a film, a gas, a gel, a globule, a granule, a chewing gum, an implant, an inhalant, an injection, an insert, an intrauterine device, an irrigant, a jelly, a kit, a liniment, a lipstick, a liquid, a lotion, a lozenge, a mouthwash, an oil, an ointment, a paste, a pastille, a patch, a pellet, a pill, a plaster, a poultice, a powder, a ring, a rinse, a salve, a shampoo, a soap, a solution, a sponge, a spray, a stick, a strip, a suppository, a suspension, a swab, a syrup, a tablet, a tampon, a tape, a tincture, a troche, a wafer, and/or combinations thereof.

The formulations may conveniently be presented in unit dosage form and may be prepared by any of the methods well known in the art of pharmacy. Such methods include the step of bringing into association compounds of the present application or a pharmaceutically acceptable salt or solvate thereof ("active ingredient") with the carrier, which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations suitable for oral administration may be presented as discrete units such as capsules, cachets, or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary, or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Molded tablets may be made by molding in a suitable machine a mixture of the powdered compound moistened with an inert liquid diluent. The tablets may optionally be coated or scored and may be formulated so as to provide sustained, delayed, or controlled release of the active ingredient therein.

The pharmaceutical compositions may include a "pharmaceutically acceptable inert carrier," and this expression is intended to include one or more inert excipients, which include, for example and without limitation, starches, polyols, granulating agents, microcrystalline cellulose, diluents, lubricants, binders, disintegrating agents, and the like. If desired, tablet dosages of the disclosed compositions may be coated by standard aqueous or nonaqueous techniques. "Pharmaceutically acceptable carrier" also encompasses controlled release means.

Pharmaceutical compositions may also optionally include other therapeutic ingredients, anti-caking agents, preservatives, sweetening agents, colorants, flavors, desiccants, plasticizers, dyes, and the like. Any such optional ingredient must be compatible with the compounds of the present application to ensure the stability of the formulation. The composition may contain other additives as needed including, for example, lactose, glucose, fructose, galactose, trehalose, sucrose, maltose, raffinose, maltitol, melezitose, stachyose, lactitol, palatinite, starch, xylitol, mannitol, myo-inositol, and the like, and hydrates thereof, and amino acids, for example, alanine, glycine and betaine, and peptides and proteins, for example, albumen.

Examples of excipients for use as the pharmaceutically acceptable carriers and the pharmaceutically acceptable inert carriers and the aforementioned additional ingredients include, but are not limited to, binders, fillers, disintegrants, lubricants, anti-microbial agents, and coating agents.

Compositions for inhalation or insufflation include solutions and suspensions in pharmaceutically acceptable, aqueous or organic solvents, or mixtures thereof, and powders. Liquid dosage forms for oral administration include pharmaceutically acceptable emulsions, microemulsions, solutions, suspensions, syrups and elixirs. In addition to the subject composition, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, cyclodextrins and mixtures thereof.

Suspensions, in addition to the subject composition, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing a subject composition with one or more suitable non-irritating excipients or carriers comprising, for example, cocoa butter, polyethylene glycol, a suppository wax or a salicylate, and which is solid at room temperature, but liquid at body temperature and, therefore, will melt in the body cavity and release the active agent.

Pharmaceutical compositions suitable for parenteral administration comprise a subject composition in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and non-aqueous carriers which may be employed in the pharmaceutical compositions include water, ethanol, polyols (such as glycerol, propylene glycol, polyethylene glycol, and the like), and suitable mixtures thereof, vegetable oils, such as olive oil, and injectable organic esters, such as ethyl oleate and cyclodextrins. Proper fluidity may be maintained, for example, by the use of coating materials, such as lecithin, by the maintenance of the required particle size in the case of dispersions, and by the use of surfactants.

Dosage forms for transdermal administration of a subject composition includes powders, sprays, ointments, pastes, creams, lotions, gels, solutions, patches and inhalants. The active component may be mixed under sterile conditions with a pharmaceutically acceptable carrier, and with any preservatives, buffers, or propellants which may be required.

The ointments, pastes, creams and gels may contain, in addition to a subject composition, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays may contain, in addition to a subject composition, excipients such as lactose, talc, silicic acid, aluminum hydroxide, calcium silicates and polyamide powder, or mixtures of these substances. Sprays may additionally contain customary propellants, such as chlorofluorohydrocarbons and volatile unsubstituted hydrocarbons, such as butane and propane.

Compositions and compounds may alternatively be administered by aerosol. This is accomplished by preparing an aqueous aerosol, liposomal preparation or solid particles containing the compound. A non-aqueous (e.g., fluorocarbon propellant) suspension could be used. Sonic nebulizers may be used because they minimize exposing the agent to shear, which may result in degradation of the compounds contained in the subject compositions. Ordinarily, an aqueous aerosol is made by formulating an aqueous solution or suspension of a subject composition together with conventional pharmaceutically acceptable carriers and stabilizers. The carriers and stabilizers vary with the requirements of the particular subject composition, but typically include non-ionic surfactants (Tweens, Pluronics, or polyethylene glycol), innocuous proteins like serum albumin, sorbitan esters, oleic acid, lecithin, amino acids such as glycine, buffers, salts, sugars, or sugar alcohols. Aerosols generally are prepared from isotonic solutions.

Dose ranges for adult humans may vary. The precise amount of the compound administered to a patient will be the responsibility of the attendant physician. However, the dose employed will depend on a number of factors, including the age and sex of the patient, the precise disorder being treated, and its severity. Similar considerations need to be utilized in conjunction with dosages for animals, including non-human mammals.

A daily dosage unit (e.g., an oral dosage unit) can include from, for example, 1 to 30 mg, 1 to 40 mg, 1 to 100 mg, 1 to 300 mg, 1 to 500 mg, 1 to 1,000 mg, 1 to 1,500 mg, 1 to 2,000 mg, 1 to 2,500 mg, 1 to 3,000 mg, 1 to 3,500 mg, 1 to 4,000 mg, 1 to 4,500 mg, 1 to 5,000 mg, 100 to 1,000 mg, 100 to 1,500 mg, 100 to 2,000 mg, 100 to 2,500 mg, 100 to 3,000 mg, 100 to 3,500 mg, 100 to 4,000 mg, 100 to 4,500 mg, 100 to 5,000 mg, 500 to 1,000 mg, 500 to 1,500 mg, 500 to 2,000 mg, 500 to 2,500 mg, 500 to 3,000 mg, 500 to 3,500 mg, 500 to 4,000 mg, 500 to 4,500 mg, 500 to 5,000 mg, 1,000 to 1,500 mg, 1,000 to 2,000 mg, 1,000 to 2,500 mg, 1,000 to 3,000 mg, 1,000 to 3,500 mg, 1,000 to 4,000 mg, 1,000 to 4,500 mg, 1,000 to 5,000 mg, 1,500 to 2,000 mg, 1,500 to 2,500 mg, 1,500 to 3,000 mg, 1,500 to 3,500 mg, 1,500 to 4,000 mg, 1,500 to 4,500 mg, 1,500 to 5,000 mg, 2,000 to 2,500 mg, 2,000 to 3,000 mg, 2,000 to 3,500 mg, 2,000 to 4,000 mg, 2,000 to 4,500 mg, 2,000 to 5,000 mg, 2,500 to 3,000 mg, 2,500 to 3,500 mg, 2,500 to 4,000 mg, 2,500 to 4,500 mg, 2,500 to 5,000 mg, 3,000 to 3,500 mg, 3,000 to 4,000 mg, 3,000 to 4,500 mg, 3,000 to 5,000 mg, 3,500 to 4,000 mg, 3,500 to 4,500 mg, 3,500 to 5,000 mg, 4,000 to 4,500 mg, 4,000 to 5,000 mg, 4,500 to 5,000 mg, 2 to 500 mg, 3 to 100 mg, 5 to 20 mg, 5 to 100 mg (e.g., 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 150 mg, 200 mg, 250 mg, 300 mg, 350 mg, 400 mg, 450 mg, 500 mg, 1,000 mg, 1,500 mg, 2,000 mg, 2,500 mg, 3,000 mg, 3,500 mg, 4,000 mg, 4,500 mg, 5,000 mg) of a compound described herein.

Additional information about pharmaceutical compositions and their formulation is described in *Remington: The Science and Practice of Pharmacy*, 20$^{th}$ Edition, 2000, which is hereby incorporated by reference in its entirety.

The present disclosure includes pharmaceutical or dermatological compositions containing the storage stable purified PSGA G in a suitable delivery system for administration to a human or mammal at a therapeutic or subtherapeutic dose, wherein the administration of the dose yields a physiologic or therapeutic response. These compositions, which include any of the classes of agents described herein, include storage stable agents prepared as described herein, along with an acceptable carrier. The carrier is preferably in the form of a lotion, cream, gel, emulsion, ointment, solution, suspension, foam, or paste. The compositions can be applied to a region of skin by spraying or misting a solution or suspension onto the region of skin, or spreading the lotion, cream, gel, emulsion, ointment, foam or paste onto the region of skin.

Preferences and options for a given aspect, feature, embodiment, or parameter, unless the context indicates otherwise, should be regarded as having been disclosed in combination with any and all preferences and options for all other aspects, features, embodiments, and parameters described in this application.

Another aspect of the present application relates to a process for producing a storage stable purified sulfated glycosaminoglycan. The process comprises providing a sulfated glycosaminoglycan starting material containing components below 1,000 Daltons, subjecting the sulfated glycosaminoglycan starting material to tangential flow filtration under conditions effective to reduce the amount of components below 1,000 Daltons in the starting material to produce a purified sulfated glycosaminoglycan having an average molecular weight ranging from 3,000 to 15,000 Daltons, wherein the purified sulfated glycosaminoglycan includes no more than 10 wt % of carbohydrates or other contaminants with a molecular weight below 1,000 Daltons, and recovering the purified sulfated glycosaminoglycan.

Lower molecular weight by-products and impurities can be removed through ultrafiltration or diafiltration. These lower molecular weight impurities and by-products are known to lead to discoloration of formulations containing the active ingredient and result in shortened shelf life and reduced commercial stability of formulations containing sulfated glycosaminoglycans not prepared using this added process. Furthermore, this treatment also allows the preparation of specific molecular ranges of these sulfated fragments obtained from naturally occurring glycosaminoglycans.

In some embodiments, the tangential flow filtration is carried out by ultrafiltration. Ultrafiltration involves separation of components, on the basis of molecular weight and size, to isolate the molecular weight components of interest. External pressure pushes a liquid through a semipermeable membrane that is capable of removing low molecular weight solutes. Ultrafiltration membranes are only accessible for small molecules and are defined by the molecular weight cut-off of the membrane used. Suspended solids and solutes of high molecular weight are retained in the retentate, and water and low molecular weight solutes pass through the membrane in the filtrate. This separation process is typically used for purifying and concentrating macromolecular ($10^3$-$10^6$ Da) solutions.

In some embodiments, the tangential flow filtration is carried out by diafiltration. Diafiltration is a dilution process that involves removal or separation of components of a solution based on their molecular size by using micromolecule permeable filters in order to obtain a desired molecular weight range. The term 'diafiltration' means a combination of 'dilution' and 'filtration' and involves use of a tangential flow filtration system. A buffer solution or demineralized water is added into the concentrate or retentate to make up the lost permeate water during filtration, in such a way keeping the concentration of rejected compounds (i.e., target products) constant, while diluting the unwanted small MW compounds for their gradual 'washing out' through the filtration cycles.

Diafiltration is normally performed with one batch of feed water, the retentate recycles back to the feed tank for further processing, and buffer solution or demineralized water is added in the feed tank as diluent. The way of adding the diluent can be continuous or discontinuous. Continuous diafiltration has the advantage of maintaining a stable concentration of target product in the retentate, as varying concentrations might incur molecular interactions and cause product loss consequently. In this continuous diafiltration mode, diluent is added with the same flowrate of permeate, when the produced permeate volume reaches to the same as the initial feed volume, one diafiltration volume or one diafiltration cycle is processed. The selection of membrane with a proper molecular weight cutoff (MWCO) is important. The MWCO of a membrane is regarded as the molecular weight (MW) of a specific polymeric compound which has 90% rejection on this membrane.

In some embodiments, the tangential flow filtration is carried out by size exclusion or another porous membrane. Porous membranes consist of a solid matrix with defined pores of a particular size, which can be used to separate solutes or particles by size. The separation of solutes by porous membranes depends mainly on the size of the molecule and the membrane pore size, with high selectivity obtained when the size of the solute or particle of interest is relatively larger than the size of the pore. Porous membranes with average pore diameters larger than 50 nm are classified as microporous, while those with average pore diameters between 2 and 0.2 nm are classified as microporous. Membranes with pore diameters below 0.2 nm are classified as nonporous, or dense.

The filtration process results in the preparation of a purified PSGAG as described above herein, containing less than 5,000 ppm of acetic acid at time of manufacture, and preferably less than 1,000 ppm. The purified PSGAG produced is stable when stored at room temperature in suitable primary or secondary containers, or combination thereof where the container is composed of plastic, paper, cardboard, or metal. Additionally, the storage container may be treated to remove or reduce residual air or oxygen.

In some embodiments, the purified sulfated glycosaminoglycan includes no more than 1 wt %, no more than 2 wt %, no more than 3 wt %, no more than 4 wt %, no more than 5 wt %, no more than 6 wt %, no more than 7 wt %, no more than 8 wt %, or no more than 9 wt % of carbohydrates or other contaminants with a molecular weight below 1,000 Daltons.

In some embodiments, the purified sulfated glycosaminoglycan includes no more than 20 wt % of carbohydrates or other contaminants with a molecular weight below 3,000 Daltons. In other embodiments, the purified sulfated glycosaminoglycan includes no more than 1 wt %, no more than 2 wt %, no more than 3 wt %, no more than 4 wt %, no more than 5 wt %, no more than 6 wt %, no more than 7 wt %, no more than 8 wt %, or no more than 9 wt %, no more than 10 wt %, no more than 11 wt %, no more than 12 wt %, no more than 13 wt %, no more than 14 wt %, no more than 15 wt %, no more than 16 wt %, no more than 17 wt %, no more than 18 wt %, or no more than 19 wt % of carbohydrates or other contaminants with a molecular weight below 3,000 Daltons.

In some embodiments, the purified sulfated glycosaminoglycan includes no more than 25 wt % of carbohydrates or other contaminants with a molecular weight below 5,000 Daltons. In other embodiments, the purified sulfated glycosaminoglycan includes no more than 1 wt %, no more than 2 wt %, no more than 3 wt %, no more than 4 wt %, no more than 5 wt %, no more than 6 wt %, no more than 7 wt %, no more than 8 wt %, or no more than 9 wt %, no more than 10 wt %, no more than 11 wt %, no more than 12 wt %, no more than 13 wt %, no more than 14 wt %, no more than 15 wt %, no more than 16 wt %, no more than 17 wt %, no more than 18 wt %, or no more than 19 wt %, no more than 21 wt %, no more than 22 wt %, no more than 23 wt %, or no more than 24 wt % of carbohydrates or other contaminants with a molecular weight below 5,000 Daltons.

In some embodiments, the purified sulfated glycosaminoglycan contains less than 5,000 ppm of acetic acid. In some embodiments the purified sulfated glycosaminoglycan contains less than 500 ppm, less than 1,000 ppm, less than 1,500 ppm, less than 2,000 ppm, less than 2,500 ppm, less than 3,000 ppm, less than 3,500 ppm, less than 4,000 ppm, or less than 4,500 ppm of acetic acid. In other embodiments, the purified sulfated glycosaminoglycan contains less than 5,000 ppm of acetic acid after storage at room temperature for at least 12 months following initiation of storage. In some embodiments the purified sulfated glycosaminoglycan contains less than 500 ppm, less than 1,000 ppm, less than 1,500 ppm, less than 2,000 ppm, less than 2,500 ppm, less than 3,000 ppm, less than 3,500 ppm, less than 4,000 ppm, or less than 4,500 ppm of acetic acid after storage at room temperature for at least 12 months following initiation of storage. In some embodiments, the purified sulfated glycosaminoglycan contains less than 5,000 ppm of acetic acid for at least 13 months, at least 14 months, at least 15 months, at least 16 months, at least 17 months, at least 18 months, at least 19 months, at least 20 months, at least 21 months, at least 22 months, at least 23 months, or at least 24 months following initiation of storage.

In some embodiments, the purified sulfated glycosaminoglycan maintains a white or off-white color after storage at room temperature for at least 6 months following initiation of storage. In some embodiments, the purified sulfated glycosaminoglycan maintains a white or off-white color after storage at room temperature for at least 7 months, at least 8 months, at least 9 months, at least 10 months, at least 11 months, at least 12 months, at least 13 months, at least 14 months, at least 15 months, at least 16 months, at least 17 months, at least 18 months, at least 19 months, at least 20 months, at least 21 months, at least 22 months, at least 23 months, or at least 24 months following initiation of storage.

In some embodiments, the process further comprises storing the purified sulfated glycosaminoglycan for at least 12 months storage at room temperature. In some embodiments, the process comprises storing the purified sulfated glycosaminoglycan for at least 13 months, at least 14 months, at least 15 months, at least 16 months, at least 17 months, at least 18 months, at least 19 months, at least 20 months, at least 21 months, at least 22 months, at least 23 months, or at least 24 months storage at room temperature. In some embodiments, the purified sulfated glycosaminoglycan contains less than 5,000 ppm of acetic acid for at least 12 months of storage at room temperature. In some embodiments the purified sulfated glycosaminoglycan contains less than 500 ppm, less than 1,000 ppm, less than 1,500 ppm, less than 2,000 ppm, less than 2,500 ppm, less than 3,000 ppm, less than 3,500 ppm, less than 4,000 ppm, or less than 4,500 ppm of acetic acid for at least 12 months of storage at room temperature.

In some embodiments, the purified sulfated glycosaminoglycan is stored in a container composed of plastic, paper, cardboard, or metal. In some embodiments, the container is treated to remove residual oxygen or air before, during, or after said storing.

The above disclosure is general. A more specific description is provided below in the following examples. The examples are described solely for the purpose of illustration and are not intended to limit the scope of the present application. Changes in the form and substitution of equivalents are contemplated as circumstances suggest or render expedient. Although specific terms have been employed herein, such terms are intended in a descriptive sense and not for the purposes of limitation.

EXAMPLES

The following Examples are presented to illustrate various aspects of the present application, but are not intended to limit the scope of the claimed application.

Example 1—Polysulfated Glycosaminoglycan Production

GAGs were prepared by extraction from domestic animal tracheal cartilage. Alternatively, GAGs are readily available and can be purchased from multiple commercial sources.

Step 1. Dissolving GAGs: To dissolve the GAGs, in Reactor 01, about 5 Kg of the glycosaminoglycan chondroitin sulfate (purchased from Bioiberica) was dissolved in 25 L of formamide at 60° C. The resulting solution was stirred for about 3 hours.

Step 2. Sulfonation Reaction: To sulfonate the glycosaminoglycan, a solution of about 7.5 L of chlorosulfonic acid dissolved in 15 L of formamide was pre-mixed in Reactor 02 and then added slowly to the GAG solution with stirring while maintaining the temperature under 30° C. Then the mixture was stirred for 16 hours in Reactor 01 at 30° C.

Step 3. Terminating Sulfonation Reaction: To terminate the sulfonation reaction, the reaction liquid was poured into 4 volumes of ethanol under stirring in a plastic barrel, whereupon a white precipitate was obtained.

Step 4. Dissolving the Precipitate with Water: After removing the supernatant, the precipitate from step 3 was transferred to Reactor 01, then dissolved in 50 L of purified water. The temperature was kept under 20° C.

Step 5. Neutralization: To neutralize the solution from step 4, it was immediately treated with 20% NaOH solution in Reactor 01, and the resulting solution had a pH of 9.0.

Steps 6 through 12. Fractionated Precipitation Repeatedly: The solution in step 5 was transferred to a plastic barrel. About four volumes of ethanol was added to the solution under stirring, then the solution was allowed to stand for 12 hours. The supernatant was removed, and then the precipitate was dissolved in 50 L of purified water. Four volumes of ethanol were added to the solution under stirring, and then the mixture was let stand for 12 hours. This process was repeated three times. The precipitate obtained in Step 12 was an intermediate. Samples were taken for analysis and the sulfate to carboxylate ratio and molecular weight were measured. The ratio of sulfate to carboxylate should be between 3 to 4. The average molecular weight should be between 6,500 to 12,000 Da.

Step 13. Dissolving the Precipitate with Water: The precipitate was dissolved in 50 L of purified water.

Step 14. Decolorization: To decolorize the solution, the pH was adjusted to 10 with 20% NaOH solution, then hydrogen peroxide was added to generate a solution with a final hydrogen peroxide concentration of around 0.5%. The mixture was then allowed to stand for three hours at room temperature. Samples were taken to check the color. If the color of the sample was not within specifications (colorless to slightly pale yellow), this bleaching step was repeated.

Step 15. Removing Extra Formamide: To remove formamide, the solution from step 14 was transferred to Reactor 01, its pH was adjusted to 10 with 20% sodium carbonate solution, and then the solution was heated to 60° C. with stirring for about 6 hours in Reactor 01.

Steps 16 to 18. Fractionated Precipitation Repeatedly: The solution in step 15 was transferred to a plastic barrel. About 4 volumes of ethanol was added to the solution under stirring, and then the mixture was allowed to stand for 12 hours. This process was repeated two more times.

Step 19. Dissolving the Precipitate with Water: The supernatant in the plastic barrel was removed, and the precipitate was dissolved in 50 L of purified water.

Step 20. Microfiltration: The pH of the solution was adjusted to 7.0 with 20% NaOH solution, then filtered through a 0.45 micrometer membrane with Filter 01. The filtrate was gathered in a plastic barrel.

Step 21. Precipitate with ethanol: About 3 volumes of ethanol was added to the filtrate and it was allowed to stand for about 12 hours in the plastic barrel.

Step 22. Dehydration and Drying: To dehydrate the precipitate, it was harvested and washed with anhydrous ethanol several times. Then the precipitate was dried under vacuum at 60° C. for 12 to 24 hours. Samples (intermediate 2) were taken for laboratory testing as described in Example 2. If the loss on drying was below 8%, the precipitate was mixed and sifted with a grinder mixer (100 mesh sieve).

Step 23. Packing: The product was packed in double polyethylene sterile bags under sterile conditions, then put in hermetically sealed aluminum containers.

Example 2—Production of Storage Stable, Purified Polysulfated Glycosaminoglycans An appropriate reaction vessel was charged with formamide and heated to 60° C. At this point chondroitin sulfate (1.00 kg) was added. This solution was then cooled to 10° C. and chlorosulfonic acid (2.63 kg) was added. Once this addition was complete, the reaction was heated at 40° C. for approximately 20 hours.

After this time the reaction was cooled, and its pH adjusted to 3 by addition of 50% aqueous sodium hydroxide. The resulting mass was then poured into ethanol and the mixture rapidly stirred, then filtered. The filter cake was washed with ethanol and dissolved in water. The pH was adjusted to 8.5 with additional 50% aqueous sodium hydroxide solution. Hydrogen peroxide was then added, and the mixture stirred for an additional 18 h. The reaction was diluted with water and the remaining hydrogen peroxide neutralized by portion-wise addition of sodium sulfite. The mixture was then filtered through Celite, and the filter cake washed twice with water.

The resulting filtrate was charged into a retentate tank and diluted with fresh deionized water. This solution was purified to remove ionic salts and low MW materials by tangential flow filtration (TFF). The filtration system consisted of a Pall Centrasette 5 TFF cassette holder equipped with a 0.5 m2 surface area Pall Centrasette II 1 KDa cuttoff cassette. A recirculating flow for the filtration process was established using a Masterflex I/P peristaltic pump operating between 1-3 L/min. The trans-membrane pressure was maintained between 20-40 psi and the filtrate containing salts and low MW compounds was collected at an approximate rate of 15-30 min/L. During the filtration process, fresh deionized water was added to the retentate tank at approximately the rate of filtrate collection to maintain a fixed volume. Once the retentate was free of lower molecular weight impurities, the resulting solution was evaporated at 55° C. to a volume of 5 L. Sodium chloride was added to the solution and the mixture stirred until homogeneous. Methanol was then added, followed by activated charcoal. After stirring for 30 minutes, the mixture was filtered, and pH of the filtrate adjusted to 6-7 with 50% sodium hydroxide.

Additional methanol was then added to the solution in a steady stream and the mixture was heated at 60-65° C. After cooling to 20-25° C., the resulting white suspension was filtered. The filter cake was washed with methanol and dried under vacuum to afford 700-800 g of PSGAG.

Example 3—Characterization of the PSGAG Compounds

The unique polyanionic property of polysulfated glycosaminoglycan (PSGAG) is determined by electrophoresis.

A 70 mm cellulose acetate (CA) membrane, saturated with 0.2 N hydrochloric acid is suspended with contact between the cathode and anode of an electrophoresis chamber. A test solution of PSGA G containing about 1 microgram of PSGAG is applied to the cathode end of the strip. A current of about 65 mA is applied for 65 minutes. The CA membrane is removed from the tank, then stained with a 0.1% toluidine blue solution for 5 minutes. The CA membrane is rinsed with a sufficient quantity of water to remove the excess toluidine blue. On the strip, PSGAG appears as only one violet-blue spot at a distance of approximately 3 cm from its starting point.

The cathode is the negative terminal of the electrophoresis chamber. Anionic compounds, such as PSGAG, under an applied current will migrate towards the chamber's anode (i.e., its positive terminal). The polyanionic property of PSGAG was compared to hyaluronic acid, chondroitin sulfate A, chondroitin sulfate B (dermatan sulfate), chondroitin sulfate C, heparin sulfate and keratan sulfate using electrophoresis. The results are as follows:

| SUBSTANCE | DISTANCE (CM) |
| --- | --- |
| PSGAG | 3.1 ± 0.3 (n = 12) |
| Hyaluronic Acid | 1.1 ± 0.1 (n = 2) |
| Chondroitin Sulfate A | 2.1 ± 0.0 (n = 2) |
| Dermatan Sulfate | 1.7 ± 0.0 (n = 2) |
| Chondroitin Sulfate C | 2.0 ± 0.3 (n = 2) |
| Heparin Sulfate | 2.3 ± 0.0 (n = 2) |
| Keratin Sulfate | 2.5 ± 0.1 (n = 2) |

The results demonstrate that the anionic property of PSGAG is significantly greater than that of hyaluronic acid, chondroitin sulfate A, dermatan sulfate, chondroitin sulfate C, heparin sulfate and keratan sulfate. PSGAG's strong negative charge enables it to bind to positively charged moieties of proteins.

The molecular weight distribution of PSGAG is determined by High Pressure Gel Permeation Chromatography (HP-GPC). The HP-GPC system uses a high efficiency gel filtration column packed with a bonded diol-coated silica gel with a particle size of 7 microns. The column's molecular weight range is between 100 to 50,000 Daltons. Through this column, a mobile phase consisting of a dilute solution of sodium sulfate (0.05 M) is pumped at a constant flow rate, pressure and temperature. Samples of the PSGAG are diluted to 5 mg per mL with the mobile phase and a portion of the resulting solution (10 g/L) is injected into the HP-GPC system.

As each separated substance is eluted, a refractive index detector measures the substance's peak response which is proportional to the substance's concentration. A computerized GPC software program interprets the data and calculates the relative: weight average molecular weight (Mw), number average molecular weight (Mn) and polydispersity index (MJMn) of the sample. These values are based on commercially available molecular weight standards ranging from 1,000 to 47,300 Daltons which are used to calibrate the system immediately prior to sample analysis.

Example 4—Formulation of Composition Into a Pharmaceutical Product

As a preliminary step in preparing the pain relief composition of the present disclosure, each of the components is put through a subjective quality control evaluation in which the color, smell and weight are evaluated. These results are then compared with previous samples of the same components to ensure that each are of the same quality as the previously used components.

Next, each of the components is separately filtered to remove any particulate matter contained therein. Filtering is preferably accomplished by passing the components through a Grade 2 filter.

Method to Make 100 g of 15% PSGAG Product

Step 1: Weigh out 15 g of the active ingredient (PSGAG).

Step 2: Weigh out 15 g of HRT Supreme or HRT Heavy cream or gel base.

Step 3: Measure out 50 mL of USP water or the equivalent purified water.

Step 4: Add water to beaker and warm gently from room temp to 72° F.

Step 5: Add water to appropriately sized unguator jar.

Step 6: Add PSGAG to unguator jar, cap and mix on mixer setting (approximately 3000 rpm) for 15 min.

Step 7: Once mixing is complete, open and verify the PSGAG is fully dissolved into solution. If water is not warm enough, repeat the mixing process until in solution. The solution will be faintly amber to clear in color.

Step 8: Add 15 g of a gelling/thickening agent, such as Fagron Versigel® (Fagron, Inc., St. Paul, Minn.), to the solution and mix again on the same mixer setting for another five minutes. Inspect the concentrate which should be smooth and viscous in nature much like a thick lotion.

Step 9: Add 15 g of cream base (Step 2) to concentrate and repeat the mixing on the gel setting once more for 15 minutes.

Step 10: Once mixing is complete the cream should be white in color and smooth to the touch. There should be no particulate or granulation in the cream at this point. More gelling agent may be added, and the mixing performed at this point until the cream consistency is achieved, but no more that 10% of the entire weight/volume so as to not dilute.

Example 5—10% PSGAG Containing 0.5% Lidocaine 10 grams of PSGAG powder was dissolved in water following the procedure in Example 4. To this solution was added 0.5 g of lidocaine hydrochloride and mixed until completely dissolved to afford an aqueous solution of pH 6.17. To this solution was added the gelling agent and cream base to afford 100 g of 10% PSGAG containing 0.5% lidocaine hydrochloride.

Example 6—10% PSGAG Containing 10% Methyl Salicylate 10 grams of PSGAG powder was dissolved in water following the procedure in Example 4. To this solution was added 10 g of methyl salicylate and mixed until completely dissolved to afford an aqueous solution of pH 6.35. To this solution was added the gelling agent and cream base to afford 100 g of 10% PSGAG containing 10% methyl salicylate.

Example 7—15% PSGAG Containing 0.1% BHT 15 grams of PSGAG powder was dissolved in water following the procedure in Example 4. To this solution was added 0.1 g of BHT and mixed until completely dissolved to afford an aqueous solution of pH 6.03. To this solution was added the gelling agent and cream base to afford 100 g of PSGAG containing 0/1% BHT.

Example 8—15% PSGAG Containing 0.2% Sodium Thiosulfate 15 grams of PSGAG powder was dissolved in water following the procedure in Example 4. To this solution was added 0.2 g of sodium thiosulfate and mixed until completely dissolved to afford an aqueous solution of pH 6.13 To this solution was added the gelling agent and cream base to afford 100 g of PSGAG containing 0/1% BHT.

Example 9—An Anesthetic Composition

| Ingredients | % W/W |
| --- | --- |
| PSGAG | 5.00 |
| Lidocaine Hydrochloride | 4.00 |
| Versapro Cream Base q.s.ad to make | 100.0 |

Levigate the ingredients into the base by serial dilution technique.

Example 10—an Anti-Inflammatory Composition

| Ingredients | % W/W |
| --- | --- |
| PSGAG | 2.50 |
| Hydrocortisone | 1.00 |
| Water | 20.0 |
| Versabase Cream Base q.s.ad to make | 100.0 |

Mix the PSGAG with water. Incorporate into the cream base with mixing. Mix until uniform. Mix in the hydrocortisone and mix until uniform in appearance.

Example 11—A Parenteral Composition

| Ingredients | % W/W |
| --- | --- |
| PSGAG | 10.0 |
| Water | 20.0 |

Dissolve the PSGAG in the water. Pass through a suitable, sterile 0.22 micro membrane filter and aseptically fill into a suitable sterile container.

Example 12—A Topical Moisturizer Composition

| Ingredients | % W/W |
| --- | --- |
| Urea | 2.00 |
| PSGAG | 25.0 |
| Water | 28.0 |
| Canola Oil | 5.0 |
| Sorbitan Sesquioleate | 14.0 |
| Ethanol | 24.0 |

-continued

| Ingredients | % W/W |
|---|---|
| Polysorbate 80 | 1.0 |
| Dimethicone Copolyol | 1.0 |
| To Make | 100.0 |

1. An aqueous phase is prepared by combining the water and urea. The ethanol, Polysorbate 80, and dimethicone copolyol are then added to this mixture while mixing.
2. In a separate container, an oil phase is prepared by combining the canola oil with the Sorbitan Sesquioleate.
3. The oil phase is then added to the water mixture and blended to form a composition.

Example 13—An Aerosol Foam Composition

| Ingredient | % W/W |
|---|---|
| PSGAG | 1.0 |
| Laureth-4 | 3.0 |
| Phosphate Acid Buffer | 0.2 |
| Ethanol | 65.0 |
| Diethylhexyl sodium sulfosuccinate | 1.0 |
| Glycerin | 3.0 |
| Water | 22.5 |
| Propellant (Propane/Isobutane) | 4.3 |
| To Make | 100.0 |

1. Combine the materials exclusive of the propellant.
2. The concentrate mixture is then filled into an aerosol container, such as an aluminum tube.
3. The propellant is then added via conventional procedures, such as through the valve or under the cup methods of charging.

Example 14

A 66-year-old male Caucasian, retiree, suffered from worsening hip pain associated with long term osteoarthritis in both hips. The man was contemplating hip replacement surgery as an increasingly likely option. His symptoms were pain, stiffness and restricted motion. He applied a mixture of 15% PSGAG cream topically to his hips and rubbed it over the area causing pain. Following treatment like this once per day, pain subsided rather quickly, and his quality of life became much improved. The patient applied the cream once per day for the first two weeks and gradually reduced usage to every other day or less, as needed.

Example 15

A 65-year-old Caucasian female suffered from a bent meniscus in her left knee, occasionally causing severe pain (identified as 9 out of 10 on a scale of 1 to 10). She applied a mixture of 15% PSGAG cream over her knee and surrounding area, rubbing it in. After treatment, the woman reported the absence of pain within hours and resorted to occasional treatment as needed.

Example 16

The 65-year-old female from Example 15 was also suffering from hemorrhoid flare ups causing significant pain, irritation, and embarrassment. The woman applied a small amount of a mixture of 15% PSGAG cream to the area of pain once a day for 2-3 days, whereupon the hemorrhoid flare up cleared, and her pain was completely relieved.

Example 17

A 57-year-old male, suffering from chronic knee pain requiring occasional cortisone injections, treated his knee daily with a mixture of 15% PSGAG cream whereupon the pain and stiffness subsided. The man continues to use the cream as needed.

Example 18

A 28-year-old male horse jockey suffered from severe elbow pain as a result of a broken bone injury sustained while race riding. This prior injury caused chronic pain and joint stiffness. This individual was unable to find an effective treatment that alleviated his pain. After daily treatment, applying a mixture of 15% PSGAG cream to his elbow and the immediate area around it, the pain was substantially alleviated, and his range of motion increased.

Example 19

A 65-year-old male Caucasian, excellent health, had a calcified toenail, with discoloration and hardness. Topically applied a mixture of 15% PSGAG cream for two weeks, once a day and toenail showed improved color, new cuticle growth, and less calcification, resulting in improved blood flow to the extremity. Immediately following application, skin shows slight redness from increased blood flow with smoothness.

Example 20

A 46-year-old female Caucasian, excellent health, post ACL meniscus repair. Pre and post walking observation with and without cream. Post surgery applied a mixture of 15% PSGAG cream to knee before walking and observed increased mobility and pain alleviation during and following exercise.

Example 21

A 70-year-old male Caucasian, excellent health, applied a mixture of 15% PSGAG cream to hand and thumb arthritis pain. Immediate increase in mobility and pain alleviation.

Example 22

A 65-year-old male Caucasian, excellent health, applied a mixture of 15% PSGAG cream to shoulder and knee joint areas following racquet sport exercise. Immediate increase in mobility and pain alleviation.

Example 23

A middle-aged woman diagnosed with Ehlers-Danlos Syndrome was experiencing pain in her neck, hands, and elbows, as well as a hip labral tear. Upon applying the 15% PSGAG cream to the affected areas, she noted a huge improvement in her hands and hip, with highly reduced pain, and an even bigger improvement in her elbows, with almost no pain anymore. Her neck showed improvement as well.

Example 24

A 65-year-old male, occupation metal artist, experienced swelling and stiffness in finger joints and wrist after strenuous activities. Upon topical application of a "fingertip" amount of the 15% PSGAG cream to the affected areas, he noted relief within 15 minutes.

Example 25

A 31-year-old female, occupation cyber services, experienced pain and swelling in finger joints and wrist after keyboard activity. Diagnosed with "hyper mobility" by an orthopedic doctor 6 months prior to application. Upon topical application of the 15% PSGAG cream to affected areas, she noted relief within 15-30 minutes. Observed better range of motion and less stiffness and pain in joints at follow up with orthopedic doctor.

Example 26

A 45-year-old female, occupation not-for-profit management, experienced pain and stiffness in lower back. Upon topical application of the 15% PSGAG cream to affected areas, she observed relief within 15 minutes.

Example 27

A 62-year-old retired female experienced severe bruising on right thigh from a fall. Upon topical application of the 15% PSGAG cream to half of the affected area, bruising was diminished after 24 hours and gone after 72 hours. The non treated area was still a deep purple color after 72 hours.

Example 28

A 62-year-old retired female experienced arthritic fingers. After topical application of the 15% PSGAG cream to the affected area, she observed better motion and less stiffness.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:
1. A pharmaceutical composition comprising:
a polysulfated glycosaminoglycan having an average molecular weight ranging from 3,000 to 15,000 Daltons;
a skin penetrating agent, wherein said skin penetrating agent promotes transdermal penetration of said polysulfated glycosaminoglycan when applied to intact skin surfaces, and is selected from the group consisting of emulsions, primary or secondary alcohols, polyoxy ethers of fatty acids, fatty acid esters, surfactants, fatty acids, and combinations thereof; and
a pharmaceutical carrier for topical application, said pharmaceutical carrier being mixed with said polysulfated glycosaminoglycan and said skin penetrating agent.
2. The pharmaceutical composition of claim 1, wherein said polysulfated glycosaminoglycan has an average molecular weight ranging from 7,000 to 9,500 Daltons.
3. The pharmaceutical composition of claim 1, wherein said polysulfated glycosaminoglycan comprises repeating disaccharide units of N-acetylgalactosamine and glucuronic acid.
4. The pharmaceutical composition of claim 1, wherein said polysulfated glycosaminoglycan has a sulfate to carboxylate ratio between 3:1 and 4:1.

5. The pharmaceutical composition of claim 1, wherein said polysulfated glycosaminoglycan is prepared from chondroitin sulfate.
6. The pharmaceutical composition of claim 1, wherein said polysulfated glycosaminoglycan comprises mucopolysaccharide polysulfate.
7. The pharmaceutical composition of claim 1, wherein said polysulfated glycosaminoglycan comprises a purified polysulfated glycosaminoglycan.
8. The pharmaceutical composition of claim 7, wherein said purified polysulfated glycosaminoglycan is prepared by a process comprising filtration and/or precipitation.
9. The pharmaceutical composition of claim 7, wherein said purified polysulfated glycosaminoglycan has been purified by precipitation from an alcoholic solvent.
10. The pharmaceutical composition of claim 9, wherein said purified polysulfated glycosaminoglycan has been purified by precipitation from methanol.
11. The pharmaceutical composition of claim 9, wherein said purified polysulfated glycosaminoglycan has been purified by precipitation from ethanol.
12. The pharmaceutical composition of claim 7, wherein said purified polysulfated glycosaminoglycan includes no more than 10 wt % of carbohydrates or other contaminants with a molecular weight below 1,000 Daltons.
13. The pharmaceutical composition of claim 7, wherein said purified polysulfated glycosaminoglycan includes no more than 20 wt % of carbohydrates or other contaminants with a molecular weight below 3,000 Daltons.
14. The pharmaceutical composition of claim 7, wherein said purified polysulfated glycosaminoglycan includes no more than 25 wt % of carbohydrates or other contaminants with a molecular weight below 5,000 Daltons.
15. The pharmaceutical composition of claim 7, wherein said purified polysulfated glycosaminoglycan contains less than 5,000 ppm of acetic acid.
16. The pharmaceutical composition of claim 7, wherein said purified polysulfated glycosaminoglycan contains less than 5,000 ppm of acetic acid after storage at room temperature for at least 12 months following initiation of storage.
17. The pharmaceutical composition of claim 7, wherein said purified polysulfated glycosaminoglycan maintains a white or off-white color after storage at room temperature for at least 6 months following initiation of storage.
18. The pharmaceutical composition of claim 7, wherein said purified polysulfated glycosaminoglycan maintains a white or off-white color after storage at room temperature for at least 12 months following initiation of storage.
19. The pharmaceutical composition of claim 7, wherein said purified polysulfated glycosaminoglycan is prepared by a process comprising subjecting a polysulfated glycosaminoglycan starting material containing components below 1,000 Daltons to filtration under conditions effective to reduce the amount of components below 1,000 Daltons in the starting material to produce a purified polysulfated glycosaminoglycan having an average molecular weight ranging from 3,000 to 15,000 Daltons, wherein the purified polysulfated glycosaminoglycan includes no more than 10 wt % of carbohydrates or other contaminants with a molecular weight below 1,000 Daltons.
20. The pharmaceutical composition of claim 7, wherein said purified polysulfated glycosaminoglycan is prepared by a process comprising subjecting a polysulfated glycosaminoglycan starting material containing components below 3,000 Daltons to filtration under conditions effective to reduce the amount of components below 3,000 Daltons in the starting material to produce a purified polysulfated glycosaminoglycan having an average molecular weight ranging from 3,000 to 15,000 Daltons, wherein the purified polysulfated glycosaminoglycan includes no more than 20 wt % of carbohydrates or other contaminants with a molecular weight below 3,000 Daltons.

21. The pharmaceutical composition of claim 7, wherein said purified polysulfated glycosaminoglycan is prepared by a process comprising subjecting a polysulfated glycosaminoglycan starting material containing components below 5,000 Daltons to filtration under conditions effective to reduce the amount of components below 5,000 Daltons in the starting material to produce a purified polysulfated glycosaminoglycan having an average molecular weight ranging from 3,000 to 15,000 Daltons, wherein the purified polysulfated glycosaminoglycan includes no more than 25 wt % of carbohydrates or other contaminants with a molecular weight below 5,000 Daltons.

22. The pharmaceutical composition of claim 1, wherein said skin penetrating agent is selected from the group consisting of anionic surface-active agents, cationic surface-active agents, nonionic surface-active agents, and combinations thereof.

23. The pharmaceutical composition of claim 1, wherein said skin penetrating agent is selected from the group consisting of primary or secondary alcohols, polyoxy ethers of fatty acids, fatty acid esters and combinations thereof.

24. The pharmaceutical composition of claim 1, wherein said skin penetrating agent is an oil-in-water emulsion comprising one or more of tocopherol acetate, an aloe derivative, a silicon derivative, a chelating agent, an emulsifier, and a polyol.

25. The pharmaceutical composition of claim 1 further comprising a pharmaceutically active agent.

26. The pharmaceutical composition of claim 25, wherein said pharmaceutically active agent is selected from the group consisting of pharmaceutically acceptable free bases, salts, esters, ethers, or solvates of antibiotics, anti-infectives, antimycotics agents, steroids, cannabinoids, antihistamines, anti-inflammatory agents, antiparasitic agents, immunomodulators, antisense agents, antiviral agents, treatments for hyper- and hypo skin pigmentation disorders, anti-psoriatic agents, keratolytic agents, DNA synthesis inhibitors, cytotoxic agents, antithyroid agents, monoclonal antibody regulators, TNF alpha antagonists, immunoglobulins, metabolic regulators, antiangiogenic agents, protease inhibitors, anxiolytics, kinase regulators, cell growth regulators, enzymes, prostaglandins, peptides, analgesics, skin moisturizers, astringents, exfoliating agents, agents intended to protect the skin or modify its appearance or improve its rate of healing, and combinations thereof.

27. The pharmaceutical composition of claim 1 further comprising:

an additive selected from the group consisting of adjuvants, gelling agents, thickeners, solvents, preservatives, pH modifiers, colorants, perfumes, flavors, propellants, absorbents, adsorbents, antioxidants, antimicrobial preservatives, and combinations thereof.

28. The pharmaceutical composition of claim 1, wherein said carrier is selected from the group consisting of a transdermal tape, a transdermal patch, an ointment, a cream, a gel, a paste, a collodion composition, a foam, a rapid dissolving solid, and a lotion.

29. The pharmaceutical composition of claim 1, wherein the pharmaceutical composition comprises 0.1 to 25 wt % of said polysulfated glycosaminoglycan, 20 to 60 wt % of said skin penetrating agent, and 20 to 80 wt % of said carrier.

30. The pharmaceutical composition of claim 1, wherein the pharmaceutical composition comprises 5 to 16 wt % of said polysulfated glycosaminoglycan, 25 to 55 wt % of said skin penetrating agent, and 25 to 75 wt % of said carrier.

31. The pharmaceutical composition of claim 1, wherein said composition is in a form suitable for topical application to skin.

32. The pharmaceutical composition of claim 1, wherein said composition is in a form suitable for topical application to mucosa.

33. The pharmaceutical composition of claim 1, wherein said composition is in a form suitable for delivery by aural, oral, ophthalmic, nasal, rectal, urethral, vaginal, dermal, buccal, or sublingual routes.

34. The pharmaceutical composition of claim 1, wherein said composition is in the form of an aerosol, a chewable bar, a bead, a capsule, a cellular sheet, a chewable gel, a concentrate, a cream, an elixir, an emulsion, an enema, a film, a gel, a chewing gum, an irrigant, a jelly, a liniment, a lipstick, a liquid, a lotion, a lozenge, a mouthwash, an oil, an ointment, a paste, a pastille, a patch, a pellet, a pill, a plaster, a poultice, a powder, a ring, a rinse, a salve, a shampoo, a soap, a solution, a sponge, a spray, a stick, a strip, a suppository, a suspension, a swab, a syrup, a tablet, a tampon, a tape, a tincture, a troche, a wafer, and/or combinations thereof.

35. The pharmaceutical composition of claim 1, wherein said skin penetrating agent is an emulsion.

36. A pharmaceutical composition comprising:

a polysulfated glycosaminoglycan having an average molecular weight ranging from 3,000 to 15,000 Daltons, wherein said polysulfated glycosaminoglycan comprises less than 5 wt % of chondroitin sulfate;

a skin penetrating agent, wherein said skin penetrating agent promotes transdermal penetration of said polysulfated glycosaminoglycan when applied to intact skin surfaces, and is selected from the group consisting of emulsions, primary or secondary alcohols, polyoxy ethers of fatty acids, fatty acid esters, surfactants, fatty acids, and combinations thereof; and a pharmaceutical carrier for topical application, said pharmaceutical carrier being mixed with said polysulfated glycosaminoglycan and said skin penetrating agent.

\* \* \* \* \*